US007407814B2

(12) United States Patent
Roukes et al.

(10) Patent No.: US 7,407,814 B2
(45) Date of Patent: Aug. 5, 2008

(54) ACTIVE NEMS ARRAYS FOR BIOCHEMICAL ANALYSES

(75) Inventors: Michael L. Roukes, Pasadena, CA (US);
Scott E. Fraser, LaCanada, CA (US);
Jerry E. Solomon, Glendale, CA (US);
Michael C. Cross, Claremont, CA (US)

(73) Assignee: California Institute of Technology, Pasadena, CA (US)

( * ) Notice: Subject to any disclaimer, the term of this patent is extended or adjusted under 35 U.S.C. 154(b) by 1025 days.

(21) Appl. No.: 09/927,779

(22) Filed: Aug. 9, 2001

(65) Prior Publication Data

US 2002/0166962 A1      Nov. 14, 2002

Related U.S. Application Data

(60) Provisional application No. 60/224,109, filed on Aug. 9, 2000.

(51) Int. Cl.
*G01N 33/543* (2006.01)
(52) U.S. Cl. ..................................... 436/518
(58) Field of Classification Search ............... 436/518, 436/517, 514, 523, 524–527, 538–541, 283.1, 436/287.1, 287.9; 435/4, 6, 7.1, 7.2, 7.5, 435/7.8, 7.81–7.95, 283.1, 287.1, 287.2, 435/287.3, 287.9, 288.7; 310/311, 312, 313 R, 310/313 A, 313 B, 313 C, 313 D, 320, 321, 310/322
See application file for complete search history.

(56) References Cited

U.S. PATENT DOCUMENTS

| 5,003,815 | A   |   | 4/1991  | Martin et al.           |
|-----------|-----|---|---------|-------------------------|
| 5,282,924 | A   |   | 2/1994  | Bayer et al.            |
| 5,481,527 | A   |   | 1/1996  | Kasanuki et al.         |
| 5,559,330 | A   |   | 9/1996  | Murashita               |
| 5,736,410 | A   |   | 4/1998  | Zarling et al.          |
| 5,807,758 | A   | * | 9/1998  | Lee et al. ....... 436/526 |
| 6,006,594 | A   |   | 12/1999 | Karrai et al.           |
| 6,087,187 | A   |   | 7/2000  | Wiegand et al.          |
| 6,289,717 | B1  | * | 9/2001  | Thundat et al. ...... 73/23.2 |
| 6,545,492 | B1  | * | 4/2003  | Altmann et al. ...... 324/754 |
| 6,911,646 | B1  | * | 6/2005  | Weitekamp ........ 250/234 |

FOREIGN PATENT DOCUMENTS

| JP | 7-225233 A | 8/1995 |
| JP | 7-260782 A | 10/1995 |
| JP | 9-189701 A | 7/1997 |
| WO | WO 98/50773 | 11/1998 |
| WO | WO 00/58729 | 10/2000 |
| WO | WO 01/33226 A1 | 5/2001 |

OTHER PUBLICATIONS

Charych et al., WO 98/50773.*
Fritz et al., "Translating Biomolecular Recognition into Nanomechanics", Science, Apr. 14, 2000, pp. 316-319, vol. 288.*
Fritz et al., "Translating Biomolecular Recognition into Nanomechanics", Science, Apr. 14, 2000, pp. 316-318, vol. 288.*
Chui et al., "Independent detection of vertical and lateral forces with a sidewall-implanted dual-axis piezoresistive cantilever", Applied Physics Letters, vol. 72, No. 11, Mar. 1998, pp. 1388-1390.*
Supplemental European Search Report dated Jun. 15, 2004, European Patent Application No. 01964587.
Baselt, David R. , et al., "Biosensor based on force microscope technology", J. Vac. Sci. Technol. B 14(2), Mar./Apr. 1996, pp. 789-793; XP000613363.
Lang, H.P., et al., "An artificial nose based on a micromechanical cantilever array", Analytica Chimica Acta, vol. 393, Mar. 1999, pp. 59-65; XP000990018.
Fritz, J, et al., "Translating Biomolecular Recognition into Nanomechanics", Science, Apr. 14, 2000, pp. 316-319, vol. 288; XP000971747.
Roukes, M.L., "Nanoelectromechanical Systems", Nov. 8, 2000, Technical Digest of the 2000 Solid-State Sensor and Actuator Workshop, Jun. 4-8, 2000, pp. 1-10; XP002284418.
Craighead, H.G., "Nanoelectromechanical Systems", Science, Nov. 24, 2000, pp. 1532-1535, vol. 290; XP000941737.
PCT International Preliminary Examination Report dated Apr. 22, 2003 from corresponding International Application No. PCT/US01/41645 filed Aug. 9, 2001.
PCT International Search Report dated Feb. 21, 2002 from corresponding PCT application No. PCT/US01/41645 filed Aug. 9, 2001.
Chui, B.W., et al., "Independent detection of vertical and lateral forces with a sidewall-implanted dual-axis piezoresistive cantilever", Appl. Phys. Lett., Mar. 16, 1998, pp. 1388-1390, vol. 72. No. 11, American Institute of Physics.
Baselt, David R., et al., "A High-Sensitivity Micromachined Biosensor", Proceedings of the IEEE, Apr. 1997, pp. 672-680, vol. 85, No. 4.

(Continued)

*Primary Examiner*—Ann Lam
(74) *Attorney, Agent, or Firm*—Foley & Lardner LLP

(57) ABSTRACT

A biofunctionalized nanoelectromechanical device (BioN-EMS) for sensing single-molecules in solution by measuring the variation in the mechanical displacement of the BioN-EMS device during a binding event is provided. The biofunctionalized nanoelectromechanical device according to the invention generally comprises a nanomechanical mechanical resonator, a detector integral with the mechanical resonator for measuring the mechanical displacement of the resonator, and electronics connected to the detector for communicating the results to a user. A system of biofunctionalized nanoelectromechanical devices and a method for utilizing the biofunctionalized nanoelectromechanical device of the present invention are also provided.

26 Claims, 18 Drawing Sheets

OTHER PUBLICATIONS

Beck, R.G., et al., "GaAs/AlGaAs self-sensing cantilevers for low temperature scanning probe microscopy", Appl. Phys. Lett., Aug. 24, 1998, pp. 1149-1151, vol. 73, No. 8, American Institute of Physics.

Binnig, G., et al., "Atomic Force Microscope", Physical Review Letters, Mar. 3, 1986, pp. 930-933, vol. 56, No. 9.

Florin, Ernst-Ludwig, et al., "Adhesive Forces Between Individual Ligand-Receptor Pairs", Science, Apr. 15, 1994, pp. 415-417, vol. 264, American Association for the Advancement of Science.

Hoh, Jan H., et al., "Quantized Adhesion Detected with the Atomic Force Microscope", *J. Am. Chem. Soc.*, 1992, pp. 4917-4918, vol. 114, American Chemical Society.

Lee, Gil U., et al., "Sensing Discrete Streptavidin-Biotin Interactions with Atomic Force Microscopy", *Langmuir*, 1994, pp. 354-357, vol. 10, American Chemical Society.

Levin, Yu., "Internal thermal noise in the LIGO test masses: A direct approach", Physical Review D, Jan. 15, 1998, pp. 659-663, vol. 57, No. 2, The American Physical Society.

Meiners, Jens-Christian, et al., "Direct Measurement of Hydrodynamic Cross Correlations between Two Particles in an External Potential", Physical Review Letters, Mar. 8, 1999, pp. 2211-2214, vol. 82, No. 10, The American Physical Society.

Moy, Vincent T., et al., "Intermolecular Forces and Energies Between Ligands and Receptors", Science, Oct. 14, 1994, pp. 257-259, vol. 266, American Association for the Advancement of Science.

Sader, John Elie, "Frequency response of cantilever beams immersed in viscous fluids with applications to the atomic force microscope", Journal of Applied Physics, Jul. 1, 1998, pp. 64-76, vol. 84, No. 1, American Institute of Physics.

Viana, Mario B., "Small cantilevers for force spectroscopy of single molecules", Journal of Applied Physics, Aug. 15, 1999, pp. 2258-2262, vol. 86, No. 4, American Institute of Physics.

Whalen, Anthony D., "Detection of Signals in Noise", Chapter 1. Probability, 1971, pp. 1-26, Academic Press, New York.

Roukes et al., Power Point slides presented Jun. 5, 2000, at the 2000 Solid-State Sensor and Actuator Workshop, Jun. 4-8, 2000, pp. 1-24.

* cited by examiner

ACTIVE NEMS ARRAYS FOR BIOCHEMICAL ANALYSES

CROSS-REFERENCE TO RELATED APPLICATION(S)

This application is based on U.S. Application No. 60/224,109, filed Aug. 9, 2000, the disclosure of which is incorporated by reference.

FIELD OF THE INVENTION

This invention is generally directed to biofunctionalized nanoelectromechanical devices (BioNEMS) for enabling dynamical single-molecule force assays of solutions.

BACKGROUND OF THE INVENTION

The revolution in molecular biology provided by DNA cloning and sequencing techniques, X-ray crystallography and NMR spectroscopy has offered unprecedented insights into the molecules that underlie the life process. However, in contrast to the dramatic rate of progress in sequencing and structural approaches, there remain major stumbling blocks in applying modern molecular knowledge fully, as many of the analytical techniques presently available remain remarkably similar to those used in the relatively early days of molecular biology and biochemistry.

For example, conventional gel electrophoresis and "blotting" techniques for determining the presence and amount of a given messenger RNA (mRNA) in a cell requires vast quantities of cells ($\sim 10^9$), and 2 days to complete. Even the most advanced DNA array chip techniques require $\sim 2 \times 10^7$ cells. Accordingly, advances in fields ranging from molecular medicine and basic cell biology to environmental toxicology are being hampered by the bottleneck generated by the sensitivity and speed of these conventional analytical techniques.

A growing literature of chemical force microscopy (CFM) has shown that a modified Atomic Force Microscope (AFM) can be tailored to measure the binding force of interactions ranging from single hydrogen bonds and single receptor-ligand interactions to single covalent bonds. For example, an early study showed the force required to break a single hydrogen bond to be on the order of 10 pN and subsequent work enabled the direct measurement of receptor/ligand interactions (~50-250 pN) and DNA hybridization (~65 pN-1.5 nN). CFM has also been utilized to study conformational changes such as the deformation of the polysaccharide dextran by an applied force and have elucidated the unfolding of the protein titan (~100-300 pN). In addition to the above experiments performed with CFM, important advances have been made with optical tweezers. In particular, they have been used to study step-wise forces in biological motor motion and sub-pN polymer dynamics.

While the range of forces associated with many biochemical systems are well within the capability of AFM instrumentation to detect, there are severe limitations to the systems in which these devices can be used. For example, an AFM cantilever in solution does not have the temporal response characteristics needed to permit the binding and unbinding of biological ligands and their receptors to be followed reliably. Especially important are variation on the few μs timescale, characteristic of important classes of conformational changes in large biomolecules. High frequency response is also critical to following the stochastic nature of receptor ligand interaction. Most receptor-ligand pairs interact dynamically: binding, remaining engaged for times ranging from microseconds to seconds (depending on the exact receptor-ligand pair), and then releasing. The analysis of biomolecules is thus limited by both the vast quantities of materials required and the smearing in time inherent in even the most sensitive assays to date.

Perhaps even more significant is the substantial size of the equipment required for performing AFM/CFM, and the density limits imposed by optical detection of the probe motion. In addition, although the sensing mechanism is generally compact, even the so-called "lab on a chip" devices optical detectors are typically employed which require large, complicated support machinery, such as readers and sample preparation apparatus. These are not portable or easily reduced in size.

Third, optical tweezers employ diffraction-limited spots, hence the optical gradient forces generated are far too spatially-extended to permit direct manipulation of individual biomolecules under study. Instead, biofunctionalized dielectric beads typically having diameters in the range 0.1 to 1 μm, are used to adhere to the analytes. Accordingly, this technology is not readily scalable to nanometer dimensions or to large-scale integration.

Finally, all of the aforementioned techniques involve force sensors with active surface areas that are quite large compared to the molecular scale; hence it can be very difficult to achieve single-molecule sensing.

Accordingly, a need exists for a system and method for single molecule sensing in solution having higher sensitivity and temporal response with reduced overall size and active surface area.

SUMMARY OF THE INVENTION

The present invention is directed to a biofunctionalized nanoelectromechanical device (BioNEMS) for sensing single-molecules in solution. This can be accomplished in two distinct modes of operation. The first is "passive" and involves measuring the variation in the resonance motion of the BioNEMS device during a binding event. The second is "active" and involves driving the devices with an external signal and looking for changes in the response upon a molecular binding event. The molecular detector according to the invention generally comprises at least one nanomechanical resonator, a detector integral with the mechanical resonator for measuring the vibration of the resonator, and electronics connected to the detector for communicating the results to a user.

In one embodiment, the molecular detector comprises a solution reservoir which contains the solution to be tested, a biofunctionalized mechanical resonator arranged within the reservoir in fluid contact with the solution, and a detector integral with the resonator for detecting the resonance of the resonator. During operation, the Brownian fluctuations inherent in a non-turbulent solution drive random fluctuations in the position of the mechanical resonator. The spectral density of the solution-induced response will depend on the nature of the solution, i.e., viscosity, temperature, flow; and the geometry of and the material used to construct the mechanical resonator. A molecule binding out of solution onto the surface of the resonator will inherently change the mechanical properties of the resonator causing a variation in the response. The resonator is preferably biofunctionalized such that only specified molecules will bind thereto, such that a binding event indicates the presence of the specific molecule in the solution. The detector is engaged with the resonator to detect the response over time such that a change in the response can be measured to determine when a binding event occurs and multiple changes in the resonance can be monitored to determine the frequency of binding events for a particular sample. The measurement of a resonance change can be used to determine the absolute presence of a particular molecule in a solution, and the frequency of binding events can be utilized to determine the concentration of the molecule in a particular solution.

Any mechanical resonator or device suitable to provide mechanical response in a solution may be utilized in the present invention, such as, for example, vibrational resonators, counter rotating and rotating resonators, torsional resonators, or compound resonators. For simplicity, all such potential mechanical detection devices will be hereafter referred to as "resonators". The resonator may be made from any suitable material, such as, for example, silicon oxide, silicon, silicon carbide and gallium arsenide. The resonator may have any physical properties suitable for detection of single-molecular binding events in solution. For example, the resonator may have a thickness between about 10 nm and 1 µm, a width between about 10 nm and 1 µm, and a length between about 1 µm and 10 µm. The resonator may have a resonance motion vacuum frequency between about 0.1 and 12 MHz. The resonator may have a force constant between about 0.1 mN/m and 1 N/m. The resonator may have a Reynolds number between about 0.001 and 2.0. The resonator may have a mass loading coefficient between about 0.3 and 11. Finally, the resonator may have a force sensitivity of about $8fN/\sqrt{Hz}$ or greater.

In one embodiment of the invention, the mechanical resonator is a vibrating cantilever of simple or complex geometry. In such an embodiment, the cantilever is preferably a piezoresistive device such that the response is measured by sensing the voltage change in the cantilever over time. In such an embodiment, the molecular detector is preferably biofunctionalized with a ligand or receptor.

In another embodiment, the molecular detector further comprises a substrate disposed within the reservoir and adjacent to the resonator, where the substrate is biofunctionalized with a ligand capable of molecular interaction with the receptor, or vice-versa. Alternatively, the substrate may also be biofunctionalized with a receptor that is not capable of molecular interaction with the receptor on the resonator, but which is capable of molecular interaction with a ligand which itself is capable of molecular interaction with the receptor on the resonator.

In still another embodiment, the molecular detector comprises at least two resonators arranged adjacent to one another, wherein one of the resonators is biofunctionalized with a receptor to form a receptor resonator and at least one of the resonators adjacent to the receptor resonator is biofunctionalized with a ligand capable of molecular interaction with the receptor such that the resonators can be coupled through the ligand/receptor functionalization.

In yet another embodiment, the molecular detector comprises at least two resonators arranged adjacent to one another, wherein at least one of the resonators is a driver resonator biofunctionalized with a receptor and having a driving element capable of resonating the driver resonator at a chosen frequency or frequencies, and at least one of the resonators adjacent to the driver resonator is biofunctionalized with a ligand capable of molecular interaction with the receptor on the driver resonator such that the resonators can be coupled through the ligand/receptor functionalization.

In still yet another embodiment, the molecular detector comprises at least three resonators, including, two driver resonators comprising driving elements capable of resonating the driver resonators at a chosen frequency in antiphase to each other, and a follower resonator disposed between the two driver resonators. In such an embodiment, at least one of the driver resonators is biofunctionalized with a receptor and the follower resonator is biofunctionalized with a ligand capable of molecular interaction with the receptor on the driver resonator such that the resonators can be coupled through the ligand/receptor functionalization. In such an embodiment, the driver may be any device suitable for driving the resonator at a specified frequency, such as, for example, a piezoresistive driver device.

In still yet another embodiment, the detector is integral with the resonator. Any detector suitable for detecting the response of the resonator may be utilized, such as, for example, a piezoresistive transducer or an optical detector. In an embodiment utilizing a piezoresistive transducer, the transducer may be made of p+doped silicon.

In still yet another embodiment, the invention is directed to a system of molecular detectors as described above. In one such embodiment the molecular detector system comprises at least one microfluidic channel and at least one array of molecular detector devices disposed within the at least one microfluidic channel, wherein the array comprises a plurality of biofunctionalized nanometer-scale mechanical resonators and where each resonator has at least one detector for measuring the response motion of the resonator.

In still yet another embodiment, the invention is directed to a method of utilizing a molecular detector as described above. In one such embodiment the method of detecting a molecule of interest comprises providing a molecular detector comprising a biofunctionalized nano-scale resonator. Placing the molecular detector into a solution such that the resonator moves based on the thermal motion of the solution and such that in the presence of a species capable of molecular interaction with the biofunctionalized resonator the response of the resonator is restricted, and measuring the response of the resonator such that a change in the response of the resonator is communicated to a user.

In still yet another embodiment, the invention is directed to a method of manufacturing a molecular detector as described above. In one such embodiment the method of manufacturing the molecular detector comprises supplying a substrate, depositing a photoresist on the substrate, exposing a pattern comprising the resonator on the photoresist, etching the substrate to form the resonator, and removing the photoresist.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

A biofunctionalized nanoelectromechanical device (BioNEMS) capable of sensing single-molecules in solution by measuring the variation in the resonance motion of a BioNEMS resonator device during a binding event is described herein. The biofunctionalized nanoelectromechanical device according to the invention being henceforth referred to as a molecular detector.

Figure 1:
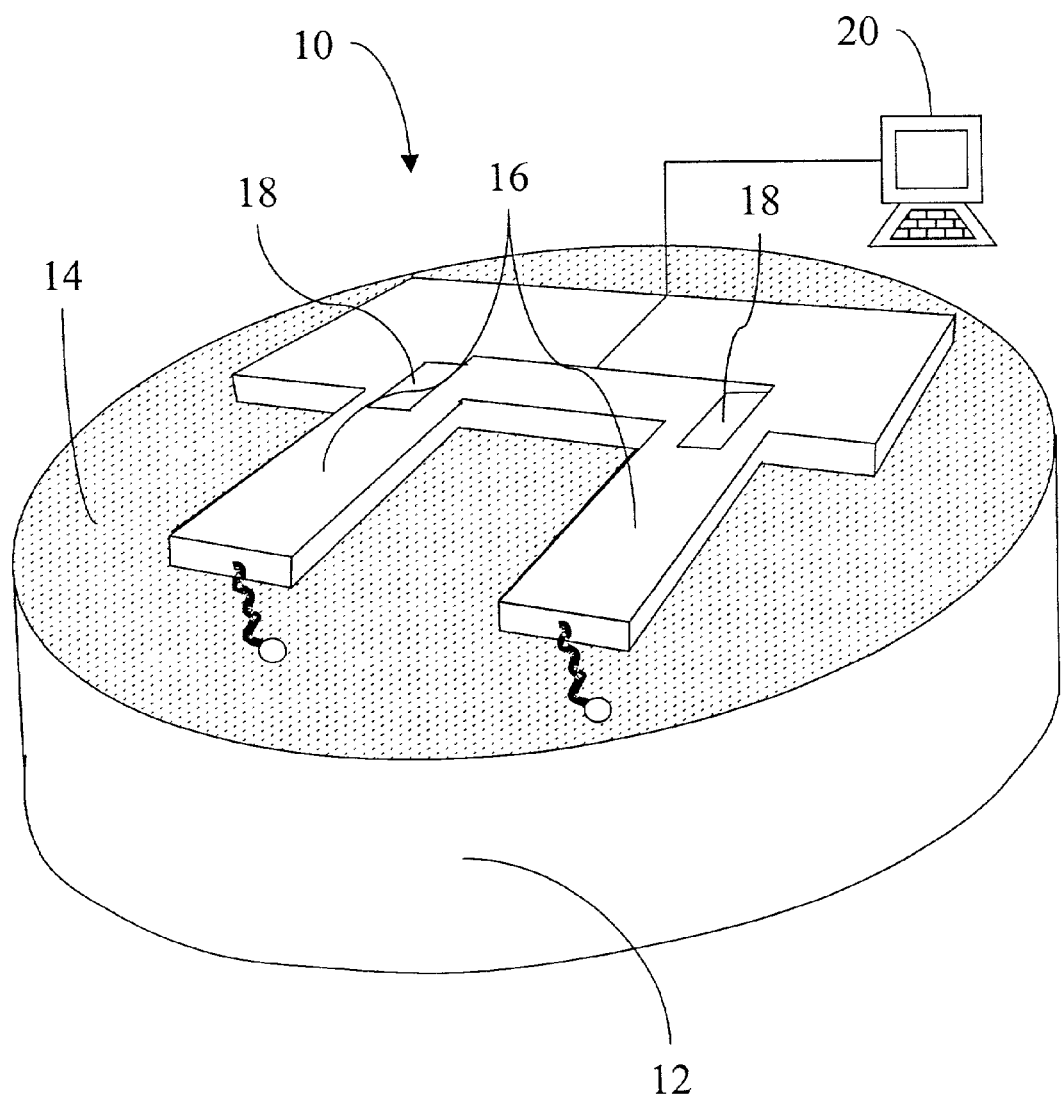
FIG. 1 is a schematic depiction of a first embodiment of a biofunctionalized nanoelectromechanical sensing device according to the present invention.
Figure 2:
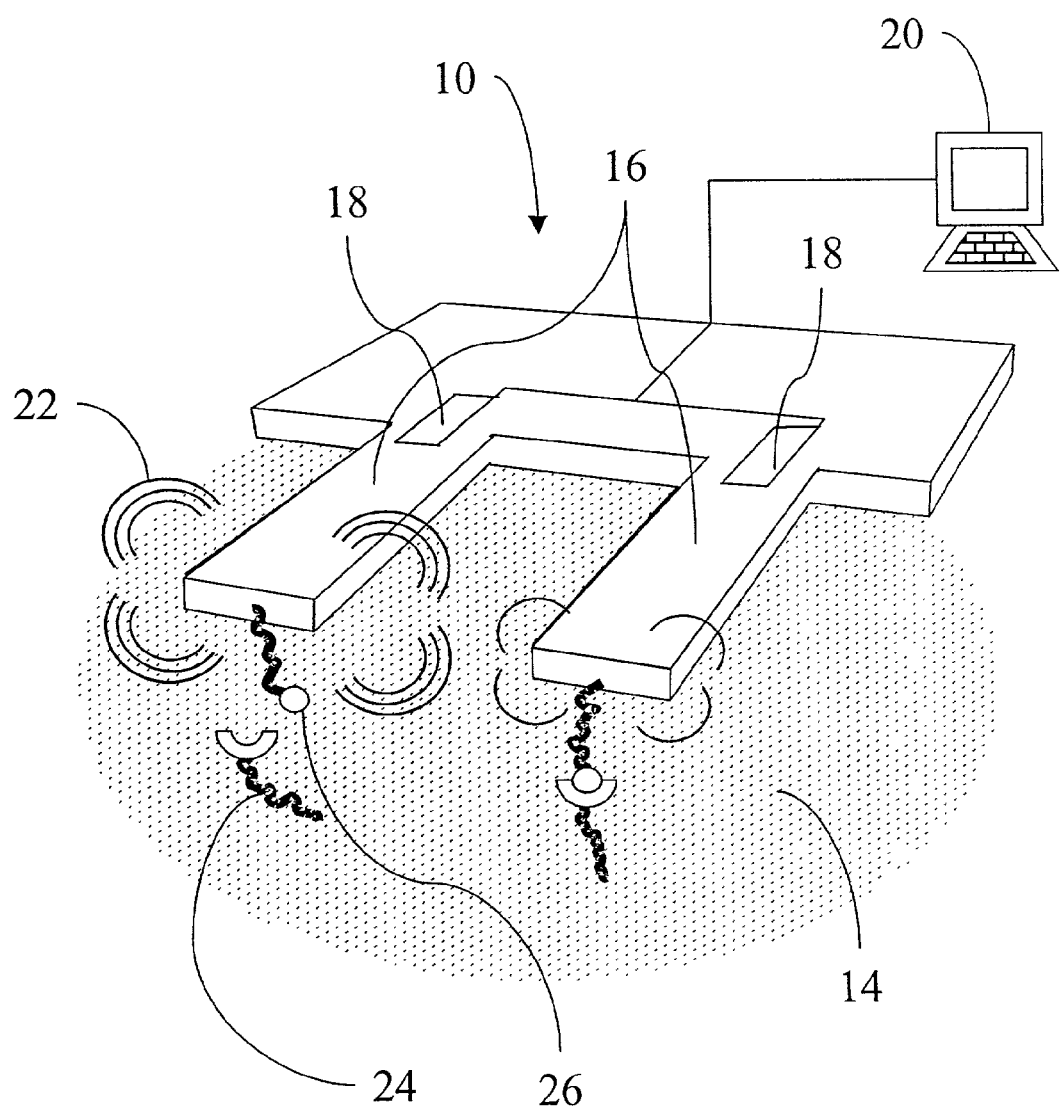
FIG. 2 is a schematic depiction of the operation of the first embodiment of a biofunctionalized nanoelectromechanical sensing device according to the present invention.

The molecular detector 10 according to one embodiment of the invention is shown schematically in FIGS. 1 and 2 and comprises a solution reservoir 12 containing a solution 14 having at least one biofunctionalized nanoelectromechanical resonator 16 arranged therein. A detector 18 in signal communication with an electronic signal processor 20 is attached integrally to the resonator 16 such that any movement by the resonator 16 is measured by the detector 18 amplified and transmitted to the processor 20.

During operation, as shown in FIG. 2, the thermal fluctuations or Brownian motion inherent in the solution 14 create mechanical displacement 22 of the position of the mechanical resonator 16, while simultaneously the presence of the solution 14 around the resonator 16 produces a dampening force on the resonance motion of the resonator 16. In the case of the vibrational cantilever resonator 16 shown in FIGS. 1 and 2, the Brownian movement of the molecules in the solution 14 create a mechanical displacement of the free end of the resonator 16. The dynamic properties of this solution-induced displacement or response 22 depends on the nature of the solution 14, i.e., viscosity, temperature, flow; and the geometry of and the material used to construct the mechanical resonator 16. Although the thermal buffeting and solution dampening of the resonator 16 makes conventional resonance detection techniques associated with AFM difficult to perform, molecules 24 binding out of solution 14 onto the surface of the resonator 16 change the mechanical properties of the resonator 16 causing a variation or restriction in the thermally induced resonance 22 and this restriction is then sensed by the detector 18 amplified and communicated to the processor 20. To ensure that the detector 18 only registers the presence of specified molecules of interest, the surface of the resonator 16 may be biofunctionalized or modified such that only specified molecules will bind thereto. For example, in FIGS. 1 and 2, the resonator 16 has been biofunctionalized with a ligand 26 chosen such that only a specified receptor molecule 24 will bind thereto. Such a modification, allows for the detection of minute quantities of specific molecules in the solution 14b utilizing the detector 10 according to the current invention.

Table 1, below displays a list of physical characteristics of a series of typical simple vibrational cantilever resonators according to FIGS. 1 and 2.

TABLE 1

Characteristics of Simple Vibrational Cantilever Resonators

| # | Thickness (t) | Width (w) | Length (l) | Vac. Freq. MHz | Force Constant (k) mN/m | $\mathfrak{R}$ | Mass Loading Coeff. |
|---|---|---|---|---|---|---|---|
| 1 | 100 nm | 1 μm | 10 μm | 1.2 | 39 | 1.884 | 3.37 |
| 2 | 30 nm | 300 nm | 3 μm | 4.1 | 12 | 0.5793 | 3.37 |
| 3 | 30 nm | 100 nm | 3 μm | 4.1 | 3.9 | 0.0644 | 1.12 |
| 4 | 10 nm | 300 nm | 3 μm | 1.4 | 0.43 | 0.1978 | 10.11 |
| 5 | 10 nm | 100 nm | 3 μm | 1.4 | 0.14 | 0.0220 | 3.37 |
| 6 | 10 nm | 100 nm | 1 μm | 12 | 3.9 | 0.1884 | 3.37 |
| 7 | 10 nm | 30 nm | 1 μm | 12 | 1.2 | 0.0170 | 1.01 |
| 8 | 10 nm | 10 nm | 1 μm | 12 | 0.40 | 0.0019 | 0.34 |

Although a simple single resonator 16 single ligand biofunctionalized 26 detector 10 is shown in FIGS. 1 and 2, any combination of resonators 16 and biofunctionalization can be utilized to create detectors 10 having unique assay properties. Examples of some exemplary molecular detectors 10 according to the current invention are shown in FIGS. 3a to 3f, and discussed below.

Figure 3A:
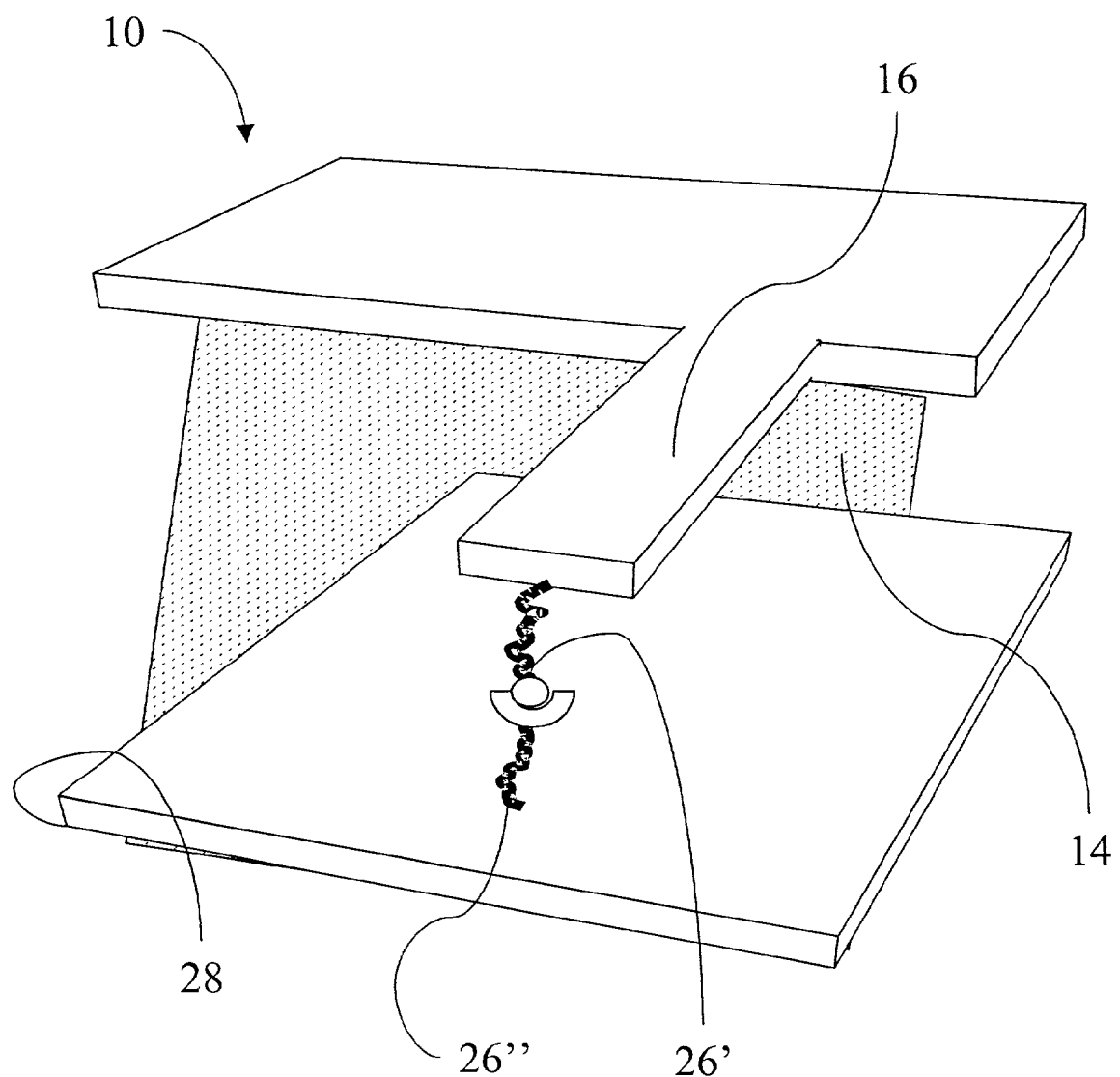
FIG. 3a is a schematic depiction of a second embodiment of a biofunctionalized nanoelectromechanical sensing device according to the present invention.

FIG. 3a shows a molecular detector 10 comprising a single resonator 16 with a ligand biofunctionalization 26' and a substrate 28 with a receptor biofunctionalization 26" designed to assay for either the presence of a free receptor or free ligand in solution or to assay for compounds that stabilize or compete with the interaction between the functional ligand/receptor. As shown, the resonator 16 will be tethered to the substrate 28 when the ligand 26' and receptor 26" interact such that the mechanical response 22 of the resonator 16 is strongly restricted.

Figure 3B:
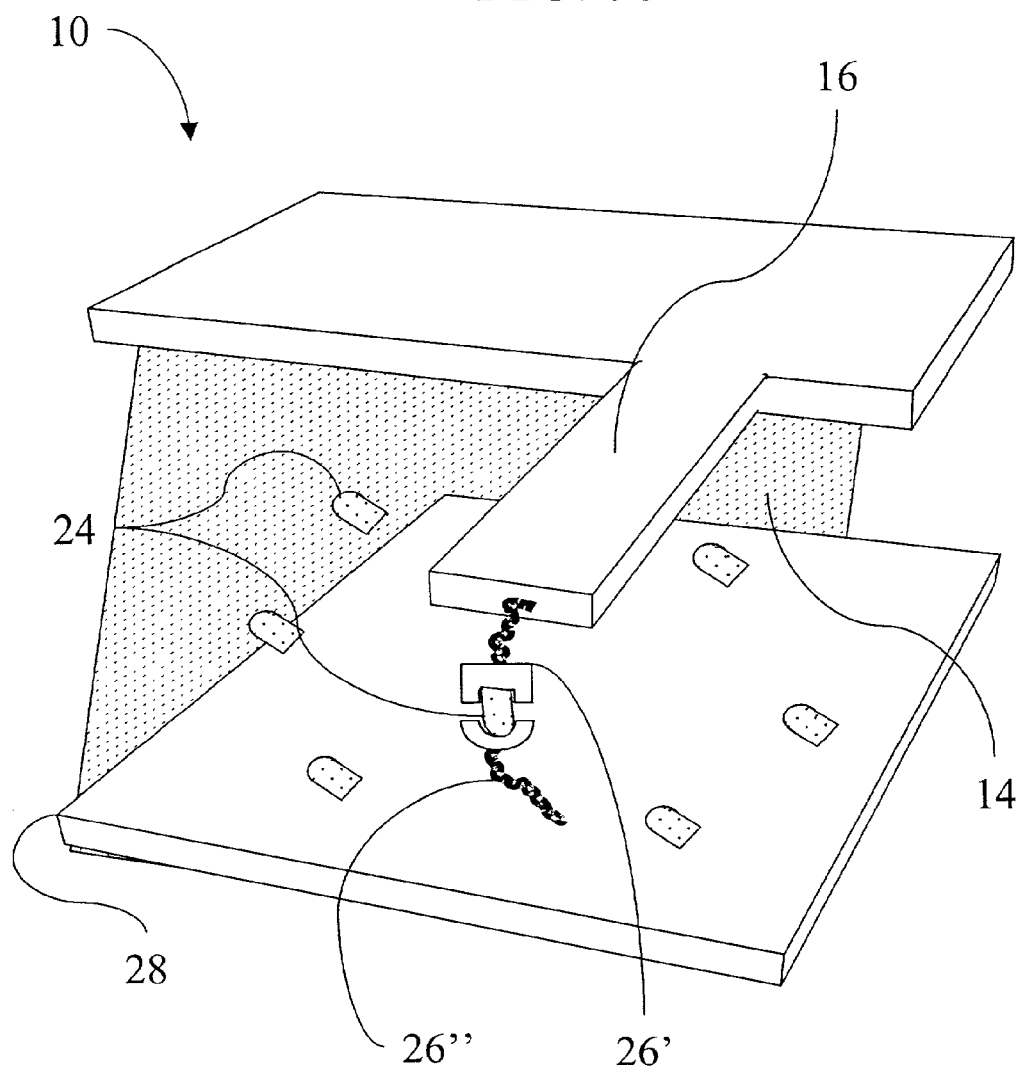
FIG. 3b is a schematic depiction of a third embodiment of a biofunctionalized nanoelectromechanical sensing device according to the present invention.

FIG. 3b shows a molecular detector 10 comprising a single resonator 16 with a receptor biofunctionalization 26' and a substrate 28 with a second receptor biofunctionalization 26" designed to assay for molecules 24 that contain target recognition sites for both receptors 26' and 26" on the same molecule.

Figure 3C:
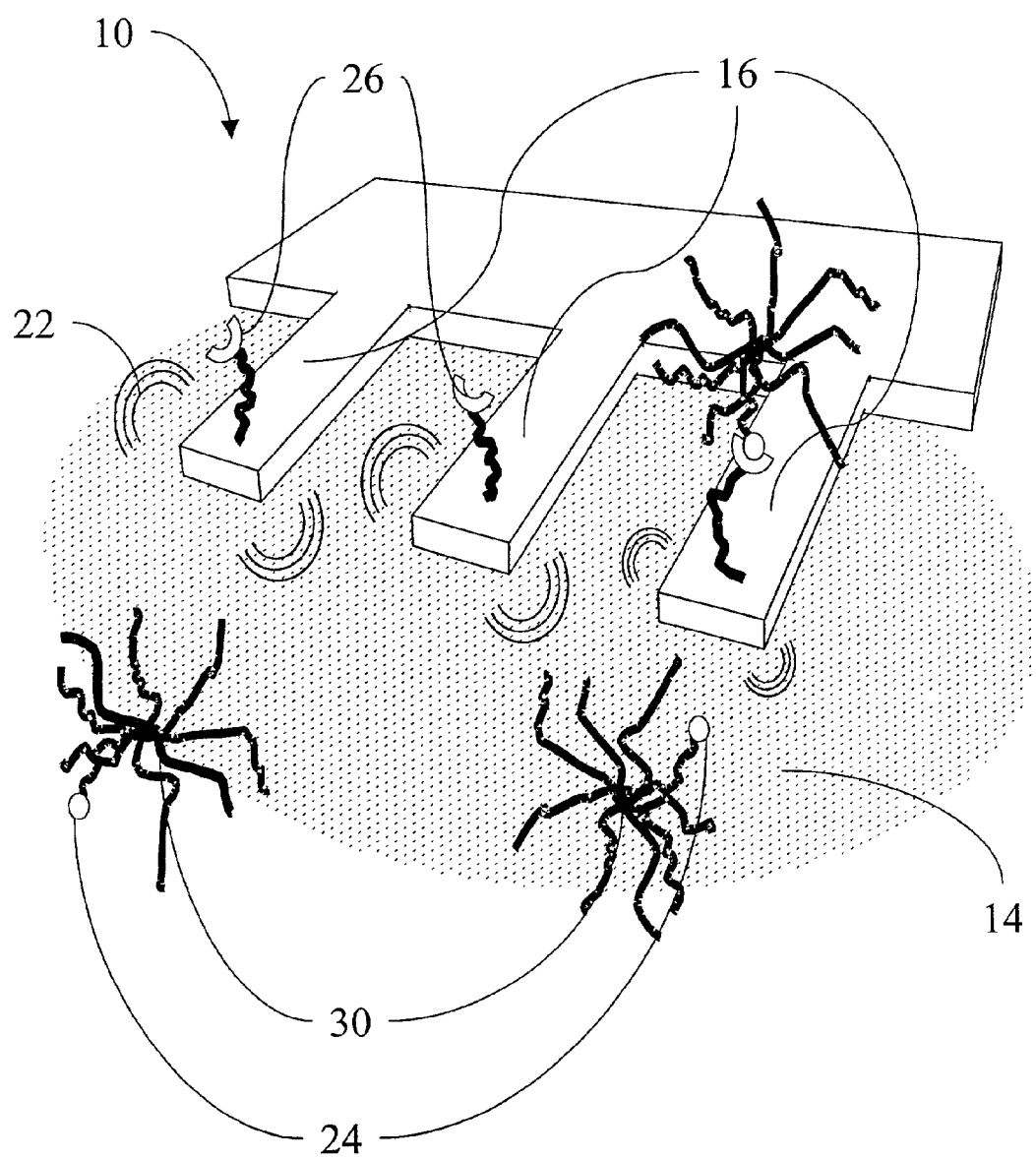
FIG. 3c is a schematic depiction of a fourth embodiment of a biofunctionalized nanoelectromechanical sensing device according to the present invention.

FIG. 3c shows a molecular detector 10 comprising multiple resonators 16 with a simple receptor biofunctionalization 26 designed to assay for single molecules 24, in which the ligand molecules 24 in the solution 14 have been modified with star dendromers 30 such that the binding of the ligand molecule 24 to the receptor biofunctionalization 26 more greatly alters the viscous drag, and therefore the mechanical response 22 of the resonator 16. Although star dendromer modifiers 30 are shown in this embodiment, any modifier which would enhance the resonator/solution coupling to provide sensitivity enhancement to the molecular detector 10 may also be utilized.

Figure 3D:
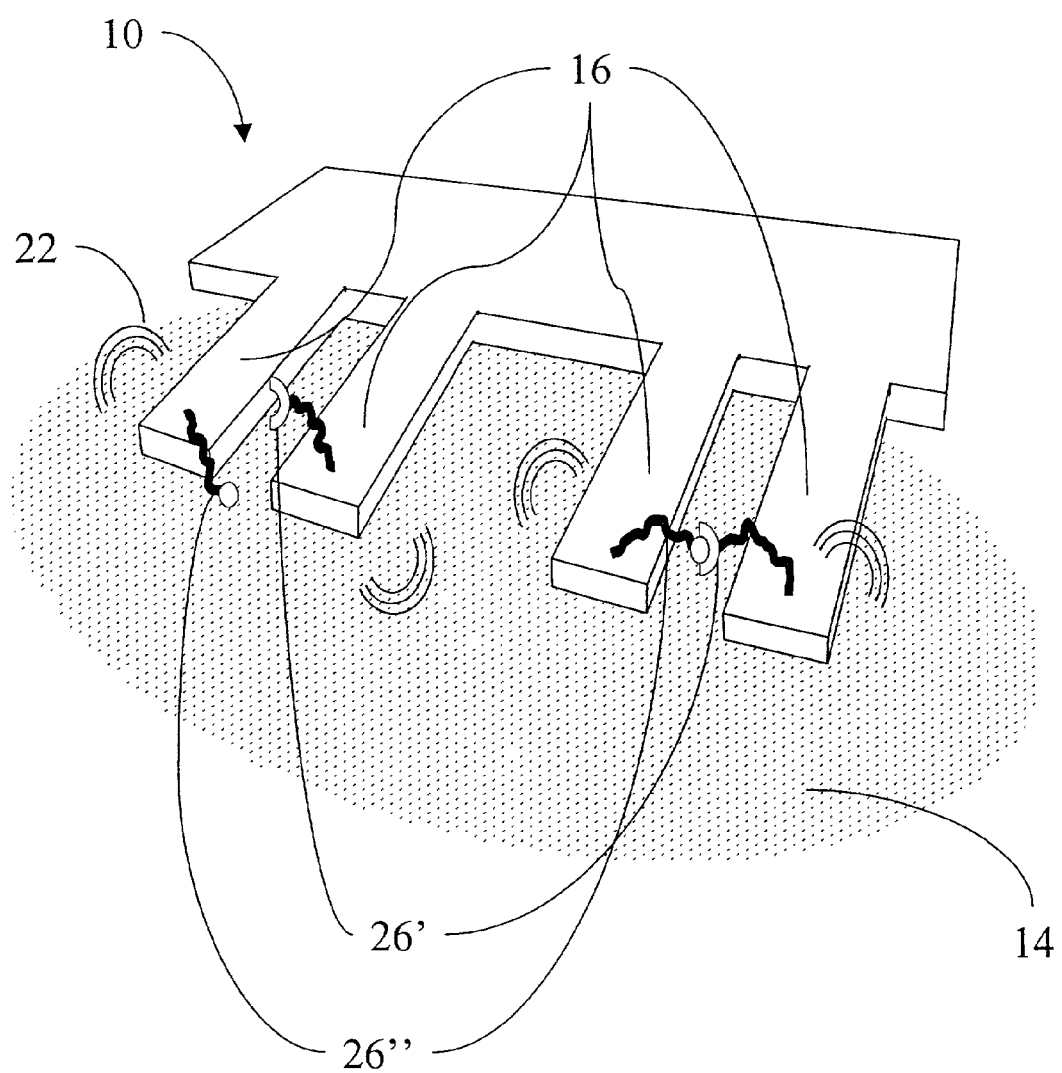
FIG. 3d is a schematic depiction of a fifth embodiment of a biofunctionalized nanoelectromechanical sensing device according to the present invention.

FIG. 3d shows a molecular detector 10 comprising multiple coupled resonators 16 with a receptor biofunctionalization 26' on one resonator 16' and a ligand biofunctionalization 26" on an adjacent resonator 16" such that the motion of the resonators 16' and 16" is coupled through the ligand/receptor biofunctionalization and such that the motion of both resonators is monitored simultaneously. In this embodiment, the correlation of the motion of the two resonators 16' and 16" allows for greater noise reduction, increasing the sensitivity of the molecular detector 10. This molecular detector 10 could be designed to assay for compounds that either bind with or stabilize or compete with the functional ligand/receptor interactions between the adjacent resonators.

Figure 3E:
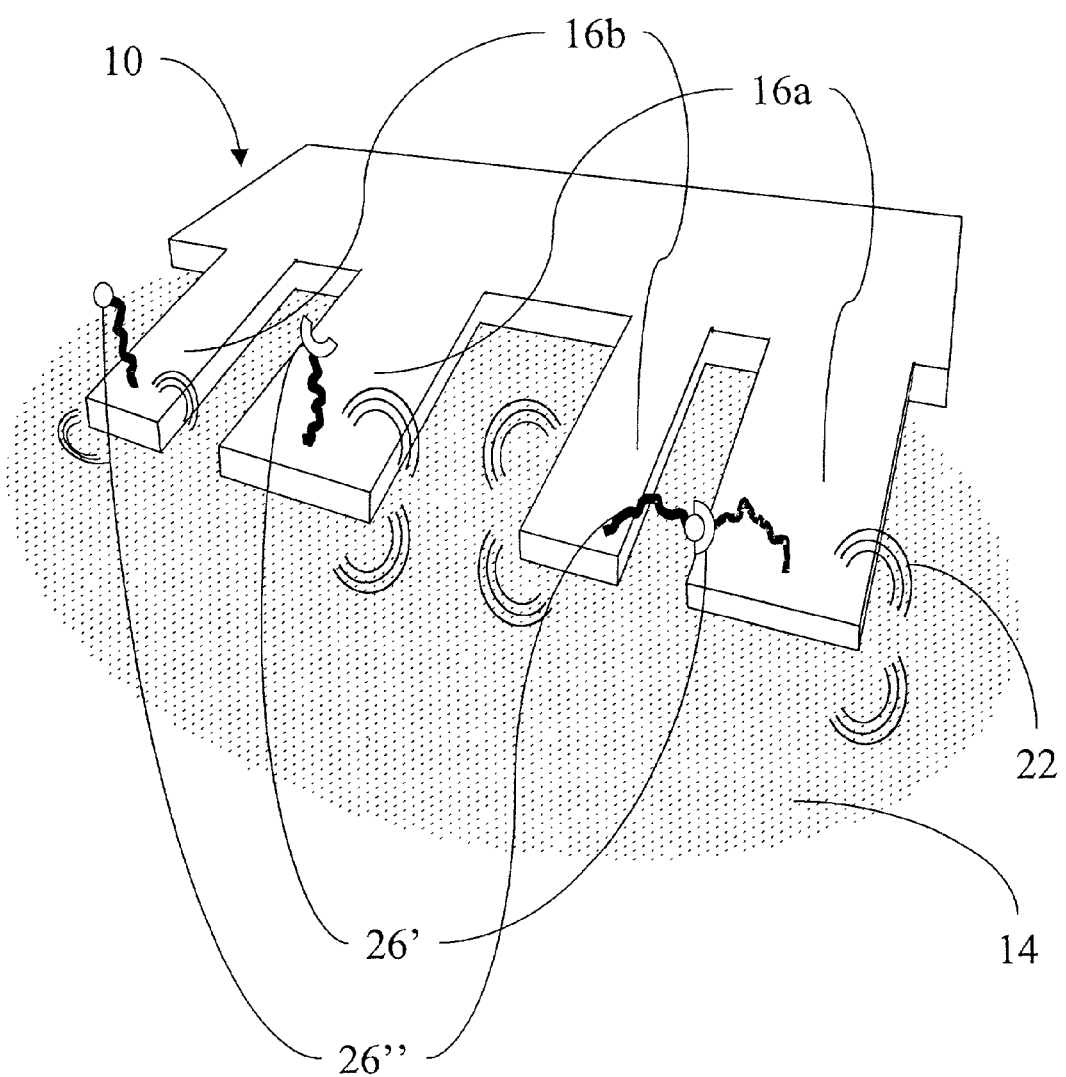
FIG. 3e is a schematic depiction of a sixth embodiment of a biofunctionalized nanoelectromechanical sensing device according to the present invention.

FIG. 3e shows a molecular detector 10 comprising at least two different resonators: a driver resonator 16a and a follower resonator 16b. As in the embodiment shown in FIG. 3d, a receptor biofunctionalization 26' is provided on the driver resonator 16a and a ligand biofunctionalization 26" is provided on the adjacent follower resonator 16b such that the motion of the resonators 16a and 16b is coupled through the ligand/receptor biofunctionalization and such that the motion of both resonators 16a and 16b is monitored simultaneously. However, in the embodiment shown in FIG. 3e a driver (not shown), actuated piezoelectrically, thermoelastically or by other physical mechanisms, actively drives the motion of the driver resonator 16a such that the motion 22 is tuned to the most sensitive amplitude and frequency possible for the geometry of the driver resonator 16a. The correlated motion of the driver resonator 16a and follower resonator 16b are then monitored to detect whether the ligand/receptor pair are functionally linked. A molecular detector 10 of this design could then be utilized to assay for compounds that either bind with or stabilize or compete with the functional ligand/receptor interactions between the adjacent resonators.

Figure 3F:
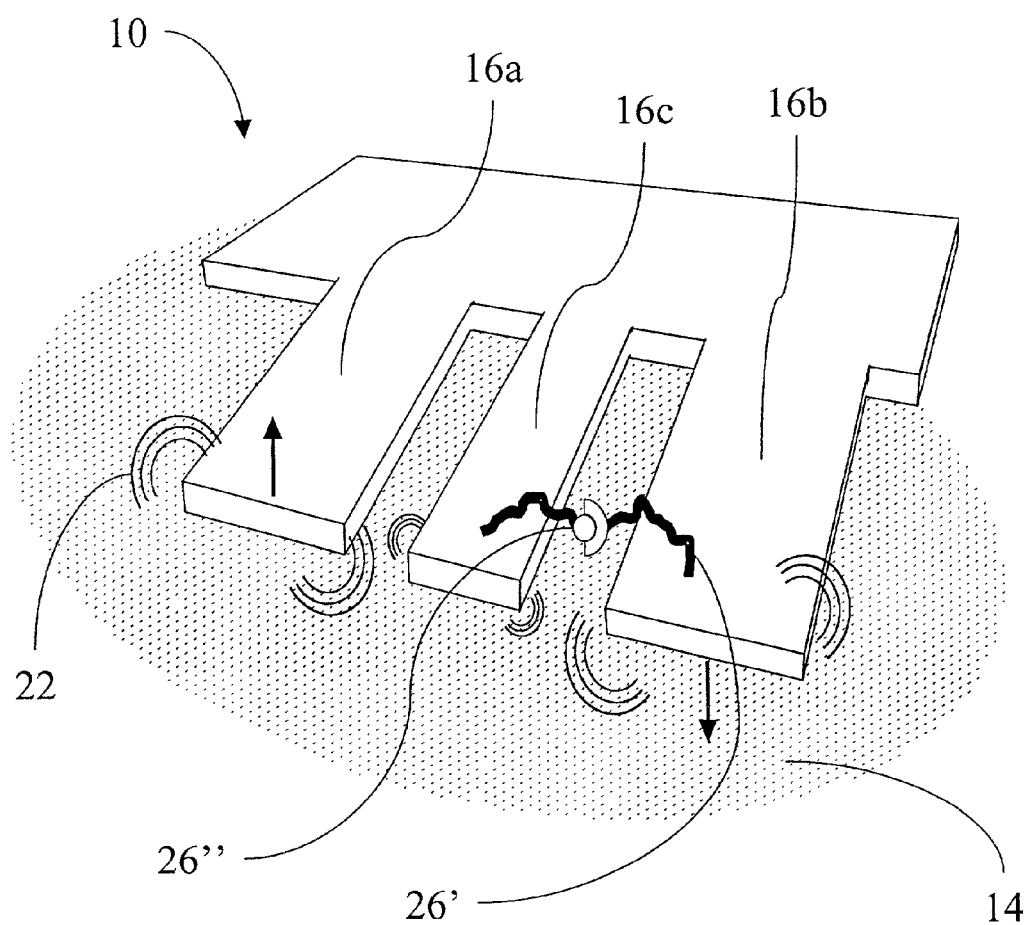
FIG. 3f is a schematic depiction of a seventh embodiment of a biofunctionalized nanoelectromechanical sensing device according to the present invention.

FIG. 3f shows a molecular detector 10 comprising at least three different resonators: a (+) driver resonator 16a, a (−) driver resonator 16b and a follower resonator 16c. As in the embodiment shown in FIG. 3e, a receptor biofunctionalization 26' is provided on one of the driver resonators 16a and a ligand biofunctionalization 26" on the adjacent follower resonator 16c such that the motion of the resonators 16a and 16c is coupled through the ligand/receptor biofunctionalization and such that the motion of both resonators 16a and 16c is simultaneously monitored. As in the embodiment shown in FIG. 3e a piezoelectric driver (not shown) actively drives the resonance motion of the driver resonators 16a and 16b such that the motion is tuned to the most sensitive amplitude and frequency possible for the resonator geometry. The correlated motion of the driver resonator 16a and follower resonator 16c are then monitored to detect whether the ligand/receptor pair are functionally linked. However, in the actively driven embodiment shown in FIG. 3e, hydrodynamic coupling between the resonators 16a and 16c may limit the dynamic range of the molecular detector 10. Providing a second active resonator 16b, operated in antiphase, nulls the hydrodynamic coupling, thereby improving the signal/noise of the molecular detector 10 thus produced. A molecular detector 10 of this design could then be utilized to assay for compounds that either bind with or stabilize or compete with the functional ligand/receptor interactions between the adjacent resonators. There may be advantages to configuring multiple-driver geometries (beyond the pair of drivers described here) to provide more refined schemes for nulling the background fluidic coupling to the "detector" cantilever.

Although the embodiments of the molecular detectors 10 discussed above in relation to FIGS. 1 to 3 all describe a single molecule ligand/receptor biofunctionalization 26, it will be understood that any suitable biofunctionalization 26 may be utilized in the current invention, such as, DNA hybridization, chemical bonds and protein unfolding. For example, the molecular detector may by biofunctionalized to screen the products of combinatorial chemistry, or to profile gene expression in cells, or to sense the concentrations of growth factors, hormones and intracellular messengers in cell biology, or to yield information about specific blood chemistry, or as a general physiology sensor, or as a detector for exposure to pathogens or toxins either in the environment or in a patient. Likewise, although all of the exemplary embodiments shown in FIGS. 1 to 3 all show single biofunctionalized sites 26 on the resonators 16, any method of biofunctionalization or number of biofunctionalized sites may be utilized on the resonators 16 of the current invention.

Figure 4:
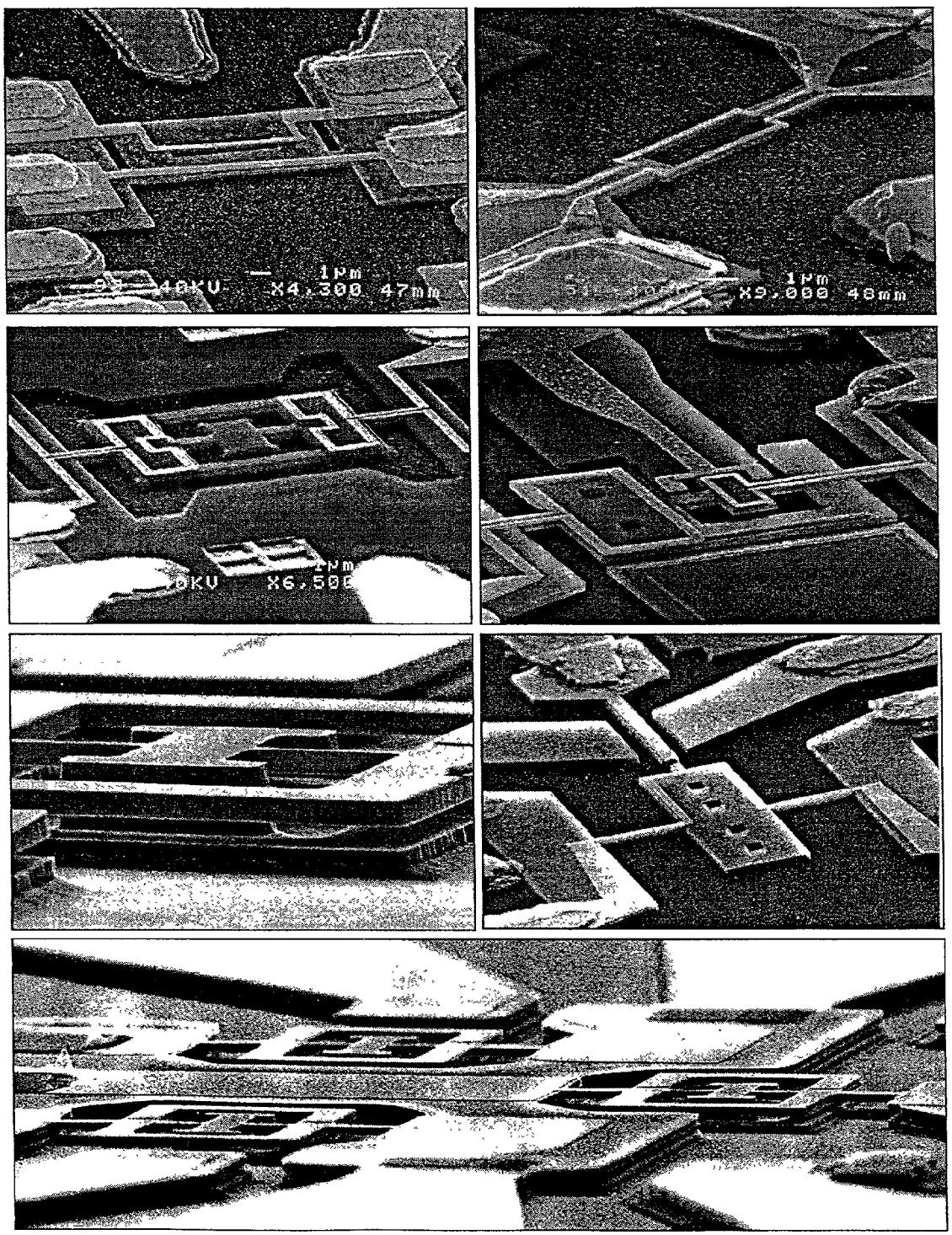
FIG. 4 is a pictorial depiction of exemplary mechanical resonators according to the present invention.

Although the embodiments of the resonator 16, shown in FIGS. 1 to 3 are all depicted as simple vibrational cantilever resonators 16, it should be understood that any NEMS construct capable of resonance motion under the thermal or Brownian motion of the solution 14, wherein the resonance is sufficiently sensitive to allow detection of a restriction in the resonance motion 22 caused by a single molecule binding event can be utilized in the present invention. FIG. 4 shows pictorial representations of several different conventional NEMS resonators 16 suitable for use in the current invention, such as, for example, rotational resonators, torsional resonators and composite resonators. In addition, it should be understood that although the resonators described above are all macrodevices, resonators comprising single molecules coupled to a substrate may be utilized according to the present invention such that the molecule itself would be modified to interact with a molecule of choice in a solution.

Figure 5:
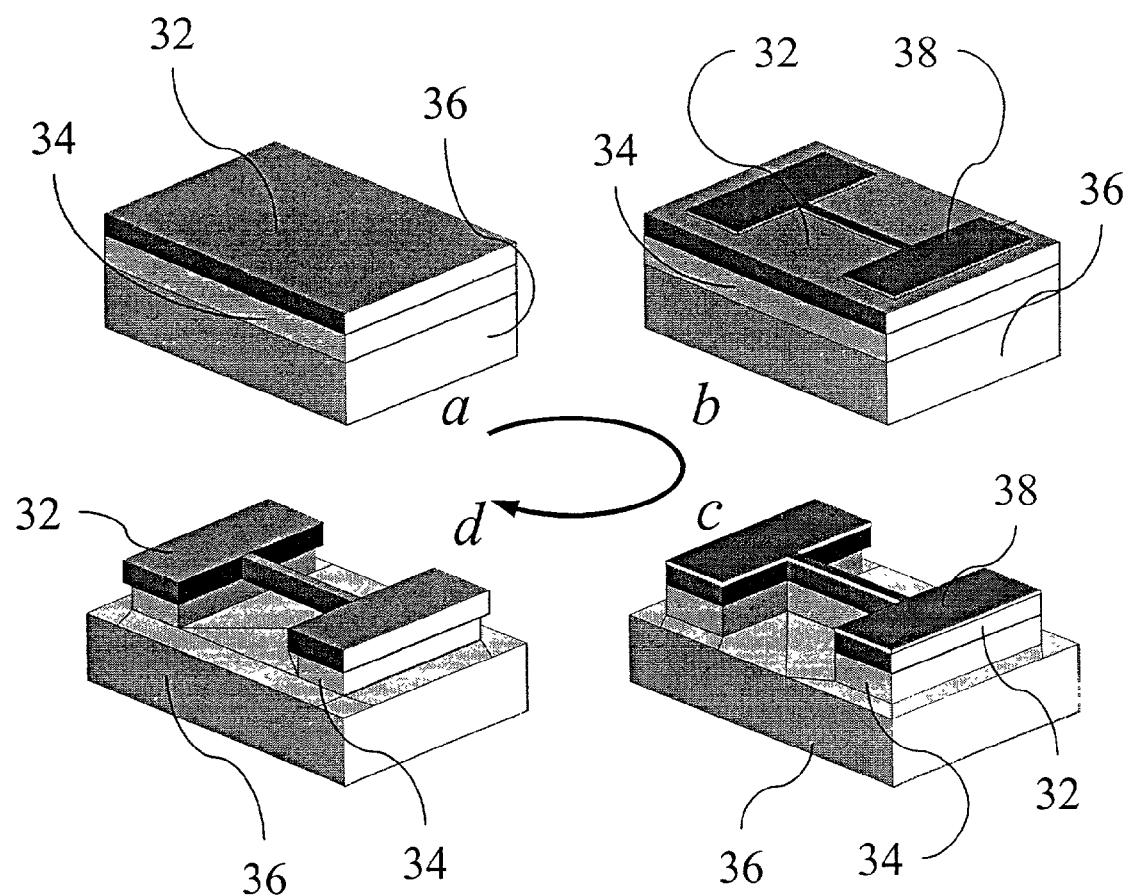
FIG. 5 is a schematic diagram of a conventional surface-etching technique for producing a biofunctionalized nanoelectromechanical sensing device according to the present invention.

The present invention is also directed to a method of manufacturing the BioNEMS molecular detector 10. FIG. 5, shows a schematic diagram of an exemplary technique for manufacturing a BioNEMS resonator 16 according to the present invention utilizing surface-etching. There are two parts to manufacturing the resonator 16 of the present invention utilizing a NEMS manufacturing method; the actual manufacturing process, and the mask design. FIG. 5, shows one embodiment of the method for making the resonator 16 according to the present invention, including the number of photolithographic steps required, and how the resonator 16 is separated from the substrate. The basic sequence, as shown, include: (a) examining and cleaning a starting substrate comprising, in the embodiment shown, three layers, a structural layer 32, a sacrificial layer 34 and a substrate layer 36; (b) modifying the surface of the structural layer 32 to form the resonator 16 via an electron beam mask 38 and depositing the photoresist and pattern resist etch metal for the resonator 16; (c) etching the pattern into the structural and sacrificial layers 32 and 34; and (d) etching the sacrificial layer 34 to undercut the resonator 16 to free the resonator 16. Although this embodiment only shows an etching process which undercuts the sacrificial layer 34, it should be understood that additional etching may be performed to create deeper undercuts and/or etching of the substrate 36 below such that insulation between the resonator 16 and the substrate 36 is increased.

While the above embodiment exemplifies a method for forming the resonator 14 of the present invention utilizing a conventional NEMS process, any manufacturing process suitable for forming the nanometer resonator 16, such as, for example, wafer bonding and etch-back may be utilized. In the wafer bonding and etch-back process a silicon wafer substrate has a very thick oxide layer deposited or thermally grown on the surface. This thick oxide layer is then covered by a thin silicon nitride layer. The resonator 16 is deposited and fabricated on this silicon nitride layer. The surface of the resonator 16 is then covered by resist, and the back of the substrate 36 is removed chemically leaving only a "frame" to support the devices. When utilizing this approach, the resonator 16 is preferably not close to the substrate 36.

The resonator 16 can be fabricated utilizing any suitable substrate material, such as, for example, silicon. In a preferred embodiment, a single-crystal silicon substrate is utilized for the resonator 16. Other silicon materials may also be utilized to make the resonator 16 of the present invention, such as, for example, thick epitaxial silicon on single crystal wafers with highly doped layers as leads, or polycrystalline silicon. Although the manufacturing process described above describes the surface nanomachining of a silicon-based material, the resonator 16 of the current invention can be made of any material suitable for surface nanomachining, capable of biofunctionalization and inert to chemical modification by and of the molecules 24 in the solution 14. Examples of conventional nanomachining materials suitable for use in the current invention include: silicon-based systems, such as silicon oxide (SOI) or silicon carbide and gallium-arsenide-based systems (GaAs). Other substrate materials may be used, as well, including insulating materials such as diamond and quartz thin films.

Any detector 18 suitable for detecting the resonance motion of the resonator 16 in solution may be utilized in the molecular detector 10 of the current invention. For example, the detector 18 may comprise vibrational or strain sensitive devices integrally connected to the resonator 16, as shown in FIGS. 1 and 2. In one exemplary embodiment the detector 18 is a piezoresistive strain transducer, as shown in FIG. 1. In this embodiment the transducer detector 18 converts the motion of the resonator 16 into an electrical signal via the strain-induced change in resistance of a conducting path on the top surface of the resonator 16. These resistance changes are then amplified and communicated to a processor 20 designed to provide a read-out of the signal changes. Although the detector 18 may be made of any suitable material, in one embodiment it is made from a p+ doped silicon epilayer formed on the top surface of the resonator 16.

Although only strain-type transducer detectors are described above, any detector suitable to monitor the motion of the resonator 16 on a time-scale suitable for monitoring the biomolecular interactions of interest may be utilized. For example, the detector 18 may also comprise an externally mounted device, such as, an optical-laser, fluorescence based position sensor, electromagnetic or magnetic.

The signal monitor system and processor 20 for any of the above detection schemes can comprise any suitable digital signal processor capable of measuring the signal change from the detector 18 and transmitting that information to the user, such as, for example, a printed circuit board having a pre-amplifier, an AD converter and driver circuit, and a programmable chip for instrumentation specific software; or a multi-chip module comprising those elements.

Regardless of the specific embodiment of the molecular detector 10 utilized, all operate on the principle that a BioN-EMS resonator will inherently posses a large thermally driven motion or mechanical response when disposed within a solution due to the repeated interaction between the resonator and the molecules of the solution, and that a chemical bond between the functionalized portion of the resonator and the molecule of interest will produce a detectable alteration of the mechanical response.

Figure 6:
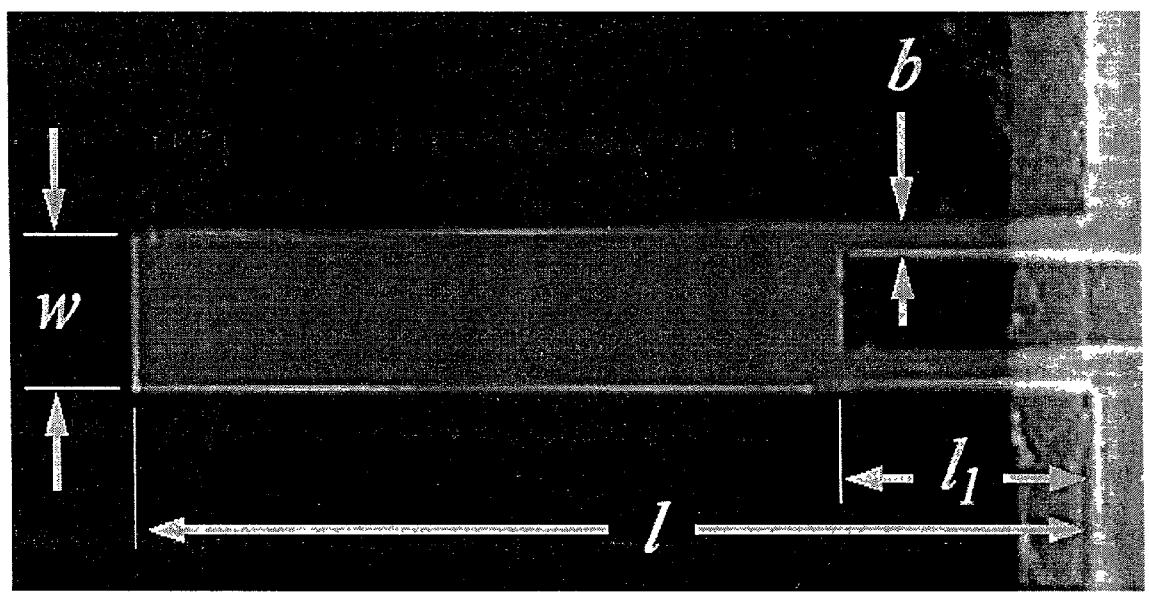
FIG. 6 is a pictorial depiction of a prototype of a biofunctionalized nanoelectromechanical sensing device according to an exemplary embodiment of the present invention.

FIG. 6 shows a prototype notched cantilever resonator 16 utilized to test the sensitivity of molecular detectors 10 made according to the present invention. First, the theoretical force sensitivity of the molecular detector 10 was calculated and then the actual performance of a series of detectors utilizing the resonator shown in FIG. 6 was tested.

Table 2, below, summarizes the physical parameters for three prototypical notched cantilever resonator 16 according to FIG. 6. Utilizing the cantilever resonator prototypes listed in Table 2 the physical properties of the molecular detector of the current invention were calculated.

TABLE 2

Characteristics of Notched Vibrational Cantilever Resonators

| # | (t) | (w) | (l) | ($l_1$) | (b) | $\omega_0/2\pi$ | K |
|---|---|---|---|---|---|---|---|
| 1 | 130 nm | 2.5 μm | 15 μm | 2.5 μm | 0.6 μm | 0.51 MHz | 34 mN/m |
| 2 | 130 nm | 300 nm | 10 μm | 2.0 μm | 100 nm | 1.3 MHz | 20 mN/m |
| 3 | 30 nm | 100 nm | 3 μm | 0.6 μm | 33 nm | 3.4 MHz | 3.0 mN/m |

Because the resonator 16 is large compared to the size of the molecules 24 in the solution 14, the thermal motion of the resonator 16 in solution 14 may be modeled in terms of stochastic forces, which are Markovian (because the time scale of the molecular collisions with the resonator are short compared to the frequencies of the macroscopic resonance motion of the resonator), and Gaussian (because the macroscopic motion is formed by a large number of molecular collisions). Accordingly, the resonance motion of the resonator 16 in the solution 14, in its fundamental mode, can be described and modeled by the fluctuation-dissipation theorem.

Any suitable calculation can be utilized to estimate this dissipation, such as, simplified geometric model estimations, low Reynolds number fluid solution calculations, or experimental measurements. The stochastic motion (x) of the resonator 16 may then be found by solving its dynamical equation with an additional fluctuating force with the spectral density. For resonators at the submicron scale in solution, as in the present invention, dissipation is dominated by the viscous motion of the fluid driven by the vibration of the resonator 16.

Because the size of the resonator 16 is much larger than the size of the individual molecules 24 in the solution 14 colliding therewith, an approximation of the force on each small section of the resonator 16 as a result of the solution 14 impinging thereon is equal to the force of the solution 14 acting on the length of an infinite beam with the same cross-section and velocity.

In the example of a single rectangular vibrational cantilever resonator 16 as shown in FIG. 1, the loading of the resonator 16 can be approximated by the Stokes equation for a cylinder according to EQ. 1, below.

$$L(\omega) = \frac{\pi \rho_L w^2}{4} \Gamma(\Re) \quad (1)$$

where the prefactor is simply the volume displaced by the resonator 16, while the function Γ, which depends solely on the Reynolds number ($\mathfrak{R}$), must be calculated from the motion of the solution 14. In this approximation, the fluidic forces from the solution 14 at each frequency and on each section of the resonator 14 are proportional to the displacement at that point.

Alternatively, a more complete calculation of the resonance motion of a resonator can be made utilizing the basic equations of motion. In the case of a notched vibrating cantilever resonator 16, as shown in FIG. 6, the equation of motion for the displacement (x) at the end of the resonator 16 is that of a simple vibrating cantilever in vacuum according to:

$$|\tilde{x}| = \frac{|\tilde{F}|}{\{[K - \omega^2 M_{eff}(\omega)]^2 + \omega^2 \gamma_{eff}^2(\omega)\}^{1/2}} \quad (2)$$

where x describes the motion of the free end of the cantilever resonator 16, F is the applied force, K is a force constant dependent on the geometry of a resonator 16 of width (w), thickness (t) and length (l). EQ. 2 provides a complete description of the resonator's 16 resonance response both to the externally applied forces and, through the fluctuation-dissipation theorem, to the stochastic forces imparted from the solution 14.

For a notched cantilever, as shown in FIG. 6, the force constant could be found according to the equation:

$$K = \frac{Et^3}{4l^3/w + (2l_1^3 - 6ll_1^2 + 6l^2l_1)\left(\frac{1}{b} - \frac{2}{w}\right)} \quad (3)$$

where (w) is the width of the end of the resonator 16, (l) is the length of the resonator 16, (t) is the thickness of the resonator 16, (b) is the width of the notch legs 30 of the resonator 16, and ($l_1$) is the length of the notched portion 32 of the resonator 16.

The equations of motion for the resonator 16 are complicated because of the presence of a dynamic solution 14 surrounding and influencing the motion of the resonator 16. Accordingly, in solution $M_{eff}$ is the effective mass of the cantilever resonator 16, which is dependent on the fluid loading of the solution 14. In vacuum the effective mass follows the equation:

$$M_{eff} \cong \alpha \rho_c wtl \left[1 + \frac{\pi}{4} T \text{Re}\{\Gamma\}\right] \quad (4)$$

which itself is dependent on the fluidic mass loading coefficient T according to:

$$T = \alpha \rho_L w/(\rho_c t) \quad (5)$$

with $\rho_L$, $\rho_C$ the density of the solution and resonator, respectively. As a result, thin resonators experience relatively large fluid loading (where $\rho_L/\rho_C=2$, T ranges from 1 to 5). The value of Re{$\Gamma$} is unity for large $\mathfrak{R}$, is around 4 at $\mathfrak{R}$ equals 1, and continues to increase as $\mathfrak{R}$ decreases. Hence, for a value of w/t equal to 2, the mass loading factor is at least 5 at $\mathfrak{R}$ equal 1, and increases for proportionally thinner beams and lower Reynolds numbers.

In turn, $\gamma_{eff}$ is the effective fluidic damping coefficient, according to EQ. 5, below.

$$\gamma_{eff} \cong \alpha \frac{\pi \rho_L}{4} w^2 l[\omega \text{Im}\{\Gamma\}] \quad (6)$$

The parameter α relates the mean square displacement along the beam to the displacement at its end. For the fundamental mode of a simple rectangular vibrational cantilever resonator 16, as shown in FIG. 1, α=0.243. In comparison, the notched vibrational cantilever resonator 16, shown in FIG. 6, α=0.333.

In addition, the term $\Gamma$ corresponds to the fluidic coupling between the resonator 16 and the solution fluid 14 according to:

$$\Gamma(\mathfrak{R}) = 1 + \frac{4iK_1\left(-i\sqrt{i\mathfrak{R}}\right)}{\sqrt{i\mathfrak{R}} K_0\left(-i\sqrt{i\mathfrak{R}}\right)} \quad (7)$$

where the Reynolds number ($\mathfrak{R}$) is given by the equation:

$$\mathfrak{R}(\omega) = \omega w^2/(4v) \quad (8)$$

where v is the kinematic viscosity of water and is equal to $1.022 \times 10^{-6}$ m²/s at 293 K.

Accordingly, for frequencies below ~1 MHz with resonators having a width less than or equal to 1 μm, the Reynolds number is less than or equal to 1.6. Thus, the damping of the resonator 16 arising from the motion of the solution 14 fluid is most dependent on the dimensions of the resonator 16 transverse to the resonance motion, e.g., in the case of a vibrational cantilever as shown in FIG. 1, the width and length of the resonator. This analysis indicates that with uniform scaling down of all dimensions, w,t,l∝d, the damping of a resonator 16 in solution 14 decreases as d with decreasing size of the resonator 16, increasing the sensitivity of the molecular detector 10.

In Table 3, below, a list of the calculated properties of the prototype notched vibrational cantilever resonators 16, as shown in FIG. 6, are provided.

TABLE 3

Characteristics of Notched Vibrational Cantilever Resonators

| # | t (nm) | w (nm) | l (μm) | $l_1$ (μm) | (b) (nm) | $\omega_0/2\pi$ (MHz) | K (mN/m) | $\mathfrak{R}$ | T |
|---|---|---|---|---|---|---|---|---|---|
| 1 | 130 | 2,500 | 15 | 2.5 | 0.6 | 0.51 | 34 | 5.0 | 8.22 |
| 2 | 130 | 300 | 10 | 2.0 | 100 | 1.3 | 20 | 0.19 | 0.986 |
| 3 | 30 | 100 | 3 | 0.6 | 33 | 3.4 | 3.0 | 0.054 | 1.42 |

As described above, the thermal noise component arises, as described by the fluctuation-dissipation theorem, from the fluidic damping of the cantilever. The mechanical Q of these structures is approximated using the equation:

$$Q \sim \frac{\omega M_{eff}}{\gamma_{eff}} \sim \frac{\text{Re}\{\Gamma(\mathfrak{R})\}}{\text{Im}\{\Gamma(\mathfrak{R})\}} \quad (9)$$

where fluid mass is assumed to dominate. It will be recognized that this expression is mostly independent of frequency, varying only over the range 0.2<Q<0.9 as the Reynolds number ($\Re$) changes from $10^{-3}$ to 1. As described above, and as expected from the calculations, the mechanical Q of these resonators 16 in the solution 14 is much less than 1, whereas their W's in vacuum are typically of on the order of $10^4$. Hence the fluidic dissipation resulting from the surrounding solution 14 completely determines the resonance 22 of the resonator 16.

To quantitatively determine the effective force sensitivity of the resonator 16 and ultimately the molecular detector 10 described by the above equations of motion, the force acting on the resonator 16 from the thermal or Brownian motion of the solution 14 must be taken into account. With this regard, the minimum detectable force is defined according to:

$$F_{min}(\omega/\omega_0) = [S_F(\omega/\omega_0)]^{1/2} \quad (10)$$

where the minimum detectable force ($F_{min}$) is defined by the force ($S_F$) acting on the resonator 16 as the result of the molecular motion of the molecules in solution 14. This stochastic force acting on the resonator 16 can be directly related to the dissipative coefficient appearing in EQ. 2, such that the force spectral density is given by the Nyquist formula:

$$S_F = 4k_B T \gamma_{eff} \quad (11)$$

where $k_B$ is Boltzmann's constant and T is the temperature of the solution 14.

Likewise, the displacement fluctuations ($S_x$) are defined by the mechanical responsivity to the spectral force ($S_F$), according to:

$$S_x^{(\gamma)}(\omega) = S_F^{(\gamma)}(\omega) R_{mech}^s(\omega) \quad (12)$$

where the mechanical responsivity $R_{mech}$ having units m/N is defined according to EQ. 13, below.

$$R_{mech} = \sqrt{R(\omega/\omega_0)}/K \quad (13)$$

where $R(\omega/\omega_0)$ is provided in analogy with Hooke's Law, $-1/K = x/F$:

$$R(f/f_0) \equiv \frac{K^2 |\tilde{x}|^2}{|\tilde{F}|^2} = \left[\left\{\frac{\omega^2}{4\omega_0^2}\left(1 + \frac{\pi}{4}\overline{T} \text{Re}\left\{\Gamma\left[\Re\left(\frac{\omega}{\omega_0} R_0\right)\right]\right\}\right) - 1\right\}^2 + \left(\frac{\pi}{16}\overline{T}\frac{\omega^2}{\omega_0^2} \text{Im}\left\{\Gamma\left[\Re\left(\frac{\omega}{\omega_0} R_0\right)\right]\right\}\right)^2\right]^{-1} \quad (14)$$

Figure 7:
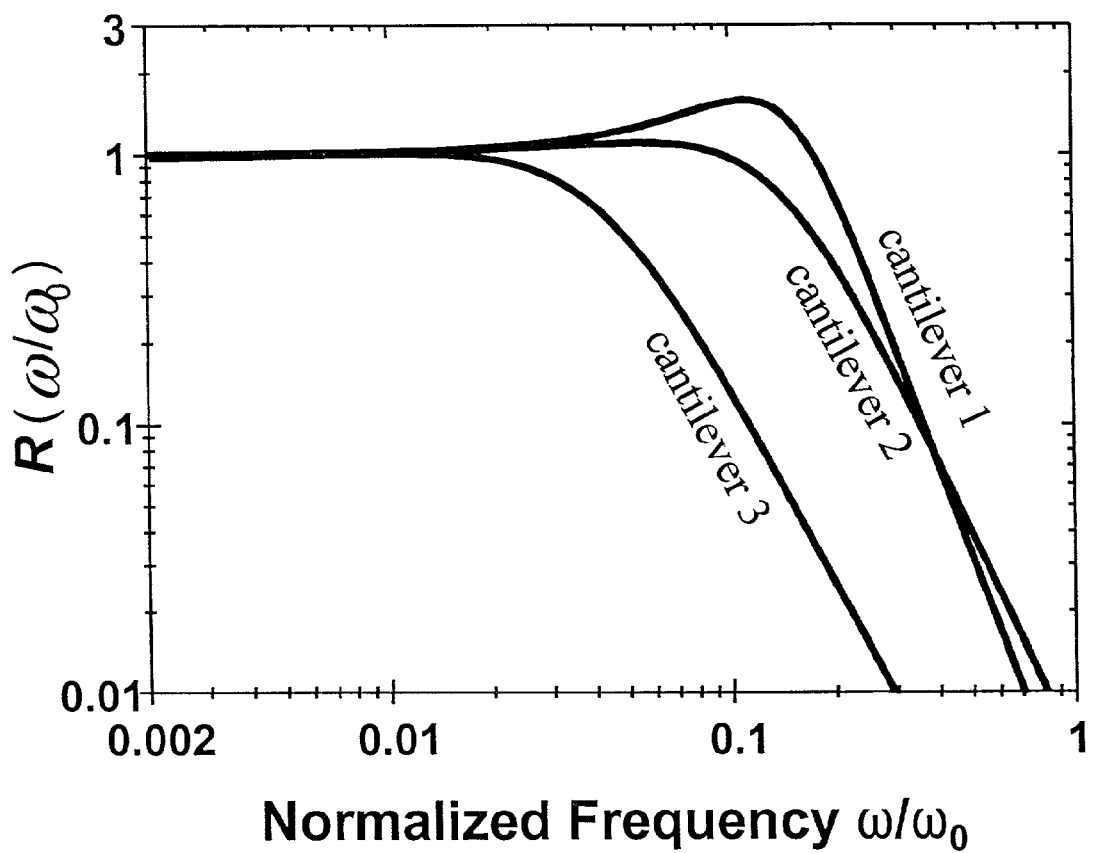
FIG. 7 is a graphical representation of the detection properties of a prototype of a biofunctionalized nanoelectromechanical sensing device according to the present invention.

In FIG. 7, the response function $R(\omega/\omega_0)$, for three different vibrational cantilever geometries is provided. It is apparent from the plot that a finite frequency peak is present in the response function of the solution damped vibrational cantilever resonators.

As described in the previous section, the frequency dependent displacement spectral density and mean square response functions obtained in the presence of fluid coupling allow an estimation of the force sensitivity attainable for different resonator geometries. However, to determine the effective force sensitivity for the molecular detector 10 according to the present invention it is also necessary to determine the noise induced by the detector 18 or the electrical noise of the system. In the three notched-vibrational cantilever resonator molecular detector prototypes 10 shown in FIG. 6 and described above, a strain sensitive piezoelectric transducer 18 was utilized to detect the resonance motion of the resonator 16. Accordingly, three additional terms are added to the real system force noise equation according to EQ. 15, below.

$$[S_F]_{eff} = \frac{1}{R_{mech}^2}\left\{[S_x]_{fluidic} + \frac{1}{R_{detector}^2}\left([S_V^{out}]_{detector}^{RTO} + [S_V^A]_{amplifier}^{RTI}\right)\right\} \quad (15)$$

In this equation $S_F$ is equivalent to the spectral force or the force fluctuations applied to the resonator 16, $S_X$ is equal to the fluid-coupled noise of the resonator 16, $S_V^{out}$ is equal to the noise generated by the detector 18, and $S_{VA}$ is equal to the noise generated by the amplifier and other processor electronics 20.

In the case of the prototype $S_V^{out}$ arises from the thermal noise of the piezoresistive transducer where $S_V^{out}$ is equal to:

$$S_V^{out} = 4k_B T R_T \quad (16)$$

while $S_{VA}$ arises from the readout amplifier's voltage and current noise according to:

$$S_{VA} = S_V + S_1 R_T^2 \quad (17)$$

where $S_V$ and $S_1$ are the spectral density of the amplifier's voltage and current noise respectively.

In those cases where the response extends down to low frequencies, a third term must also be considered, the 1/f noise ($S_{1/f}$) in the transducer. Although this term must be considered, there is a fundamental difference between the 1/f noise and that of the fluid-induce displacement fluctuations. As such, in a preferred embodiment a lock-in detection scheme is used to measure the resistance such that only the portion of the 1/f spectrum within the detection window will contribute to the noise. Alternatively, by probing the resistance at frequencies above the 1/f knee, this source of noise can be practically eliminated.

In contrast, the fluid-induced displacement fluctuation noise leads to changes in the resistance of the resonator that are within the detectable range regardless of the frequency probe current used. Hence, the entire noise spectrum from dc up to the frequency of the low pass filter is relevant.

The force sensitivity of the molecular detector 10 of the current invention, then, hinges on the maximum level of current bias that is tolerable, given that the responsivity is proportional to the bias current (R=IG), where the gauge factor (G) is equal to:

$$G = \frac{\partial R_T}{\partial x} = \frac{3\beta \pi_l (2l - l_1) R_T}{2bt^2} \quad (18)$$

and where the parameter $\pi_1$ is the piezoresistive coefficient of the p+ transducer material. The factor $\beta$ accounts for the decrease in G due to the finite thickness of the of the conducting layer; $\beta$ approaches unity as the carriers become confined to a surface layer of infinitesimal thickness.

Figure 8:
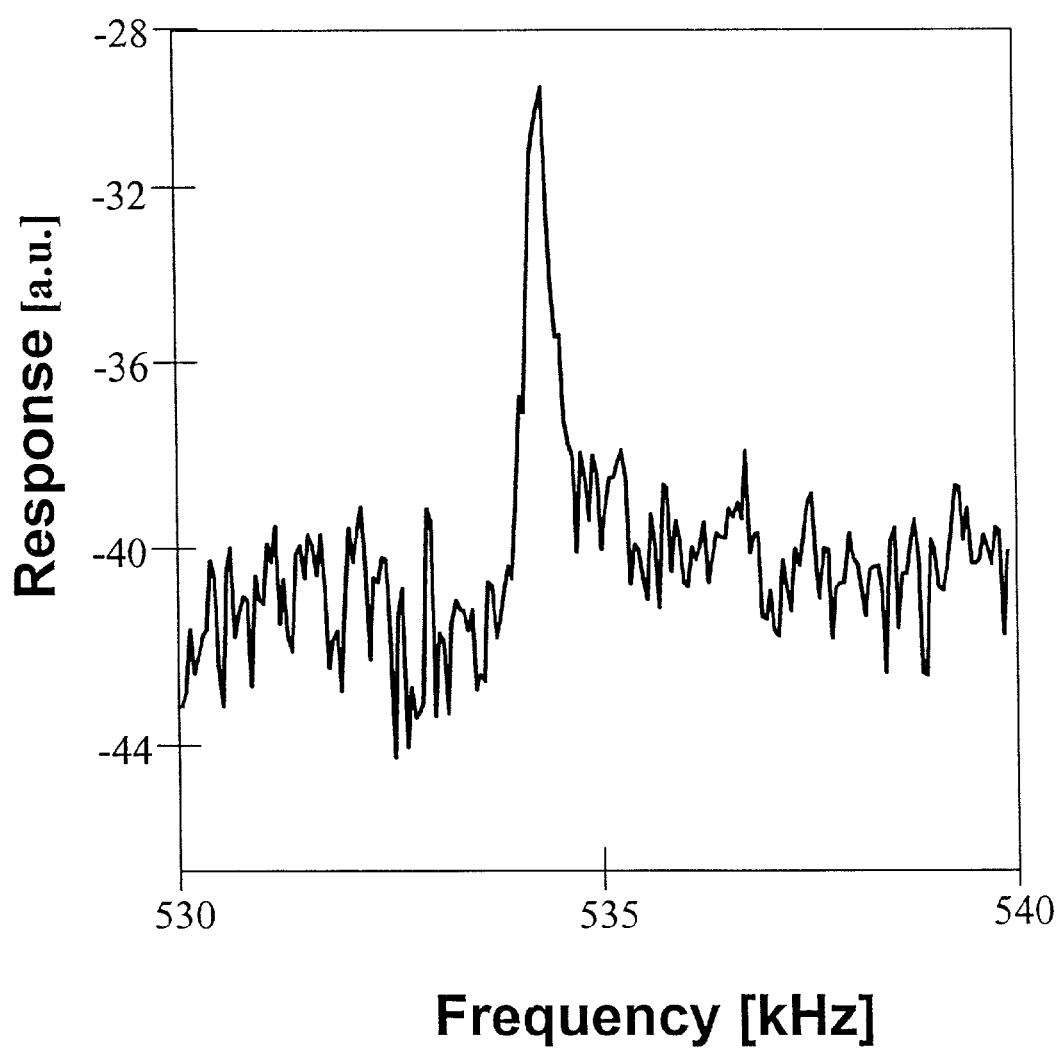
FIG. 8 is a graphical representation of the detection properties of a prototype of a biofunctionalized nanoelectromechanical sensing device according to the present invention.
Figure 9:
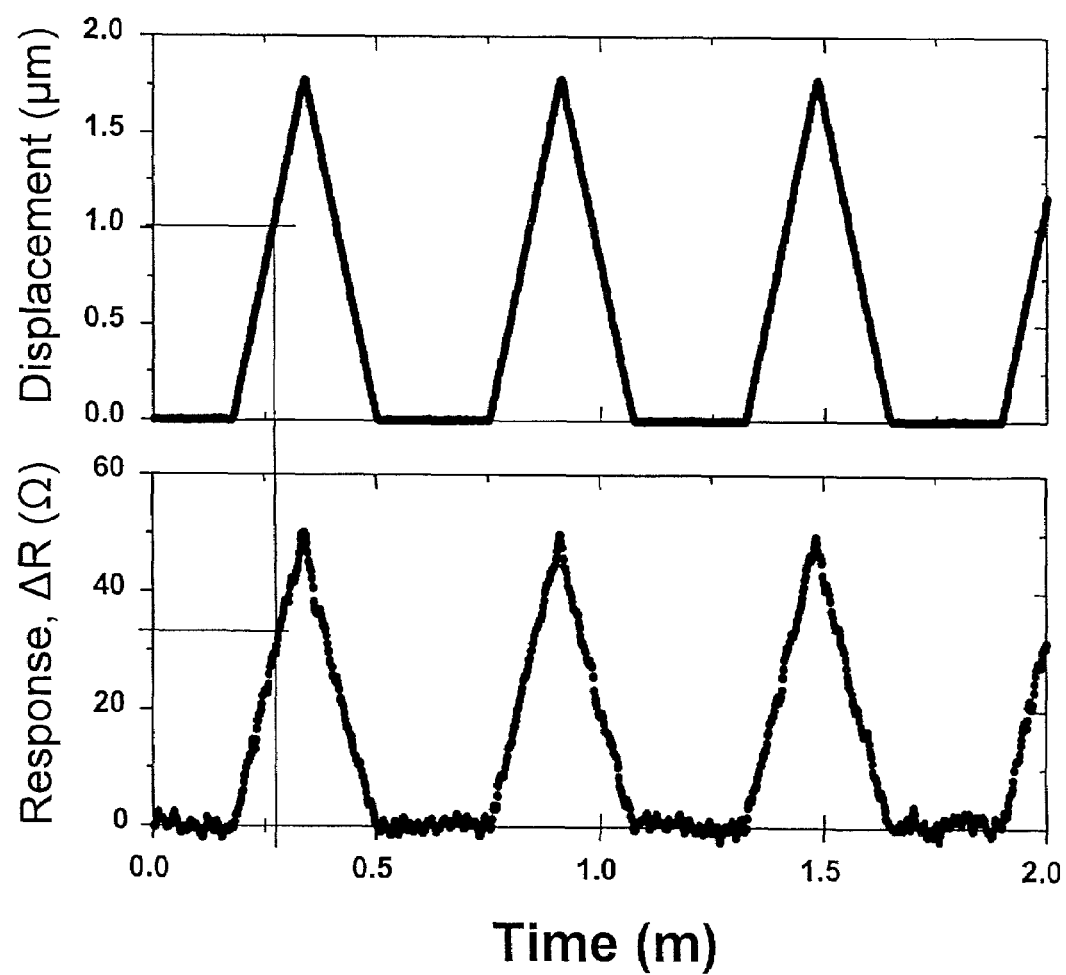
FIG. 9 is a graphical representation of the detection properties of a prototype of a biofunctionalized nanoelectromechanical sensing device according to the present invention.

To quantify some of the parameters for the prototype notched vibrational cantilever resonators shown in FIG. 6, the resonance motion and resistance of the resonators was measured. FIG. 8 shows the measured room temperature fundamental resonance motion for the first prototype cantilever resonator listed in Table 2 in vacuum. FIG. 9 shows a plot of the displacement of the prototype cantilever shown in FIG. 6 caused by the resonance motion versus resistance.

These plots yield a direct measurement of $G=3\times10^7$. For epilayers such as those used in the prototype molecular detectors shown in FIG. 6, the EQ. 18 yields a calculated value of $\beta=0.7$ and $G=6\times10^8$ $\Omega$/m. For the transducer geometry pictured in FIG. 6, a two-terminal (equilibrium) resistance of $R_T=15.6$ k$\Omega$ is obtained.

Using the values for the resistance and the gauge factor (G) above, it is possible to determine the maximum current bias, which is found by determining the maximum temperature rise deemed acceptable for the biofunctionalization disposed along the resonator. The geometry of the prototype devices shown in FIG. 6 causes dissipation to occur predominantly within the constriction regions (of width b). A rough estimate of the heat loss to the surrounding solution may be obtained through the relationship:

$$\kappa_{Si} A \frac{\partial^2 T}{\partial x^2} = \kappa_{H_2O} P \nabla_n T \quad (19)$$

where P is the perimeter around cross-sectional area A of the resonator. Estimating that:

$$\nabla_n \sim T/w \quad (20)$$

and that, $$\frac{\partial^2 T}{\partial x^2} \sim \frac{2(w+t)\kappa_{H_2O}}{\kappa_{Si} t w^2} \quad (21)$$

where $\kappa_{Si}=1.48\times10^2$ W/mK is the thermal conductivity of silicon and $\kappa_{H_2O}=0.607$ W/mK is the thermal conductivity of water. In the dissipative region $x<l_1$, $$2\kappa_{Si} tb \frac{\partial^2 T}{\partial x^2} \sim -I^2 R + (b+t)\frac{T}{b}\kappa_{H_2O} \quad (22)$$

where as boundary conditions, the temperature is continuous at $l_1$, as is the heat flux; and $\delta T/\delta x=0$ at $x=1$.

This simple thermal conductance calculation indicates that, for example, a 1 K rise a the biofunctionalized tip is attained with a steady-state bias current of 250 μA, leading to a power dissipation of roughly 10670 μW. The maximal temperature rise of 12K occurs within the constricted region, approximately 2.3 μm from the support. For this bias current, the prototype molecular detector 10 yields a responsivity of $R=IG\sim8$ μV/nm.

Utilizing these parameters, an estimated coupled force sensitivity can be determined. For cantilever 1, assuming that a 1K rise at the tip is tolerable, the transducer-induced displacement noise is found to be $\sqrt{S_{VT}}/R=1.8\times10^{-12}$ m/$\sqrt{Hz}$. For a typical low noise readout amplifier with voltage and current noise levels of ~4 nV/$\sqrt{Hz}$ and ~5 fA/$\sqrt{Hz}$, respectively (typical for JFET input low noise amplifiers) these same parameters yield an amplifier term $\sqrt{S_{VA}}/R=4.4\times10^{-13}$ m/$\sqrt{Hz}$.

To demonstrate the effects of scaling the resonator downward in size, cantilever resonators 2 and 3, having a geometry identical to that of cantilever resonator 1, are also considered. Utilizing the physical dimensions of cantilever 2 the above equations yields an $R_T=67$ k$\Omega$ and a $G=7.4\times10_9$ $\Omega$/m. For cantilever resonator 2, assuming an 0.05K temperature rise at the tip of the resonator is tolerable yields a transducer-induced displacement noise $\sqrt{S_{VT}}/R=6.3\times10^{-4}$ m/$\sqrt{Hz}$ and a readout amplifier contribution of $\sqrt{S_{VA}}/R=8.0\times10^{-15}$ m/$\sqrt{Hz}$. For cantilever resonator 3, the above equations yields an $R_T=258$ k$\Omega$ and a $G=7.39\times10_{10}$ $\Omega$/m. Again assuming an 0.05K temperature rise at the tip of the resonator is tolerable yields a transducer-induced displacement noise $\sqrt{S^{VT}}/R=3.8\times10^{-14}$ m/$\sqrt{Hz}$ and a readout amplifier contribution of $\sqrt{S^{VA}}/R=3.3\times10^{-15}$ m/$\sqrt{Hz}$.

Figure 10:
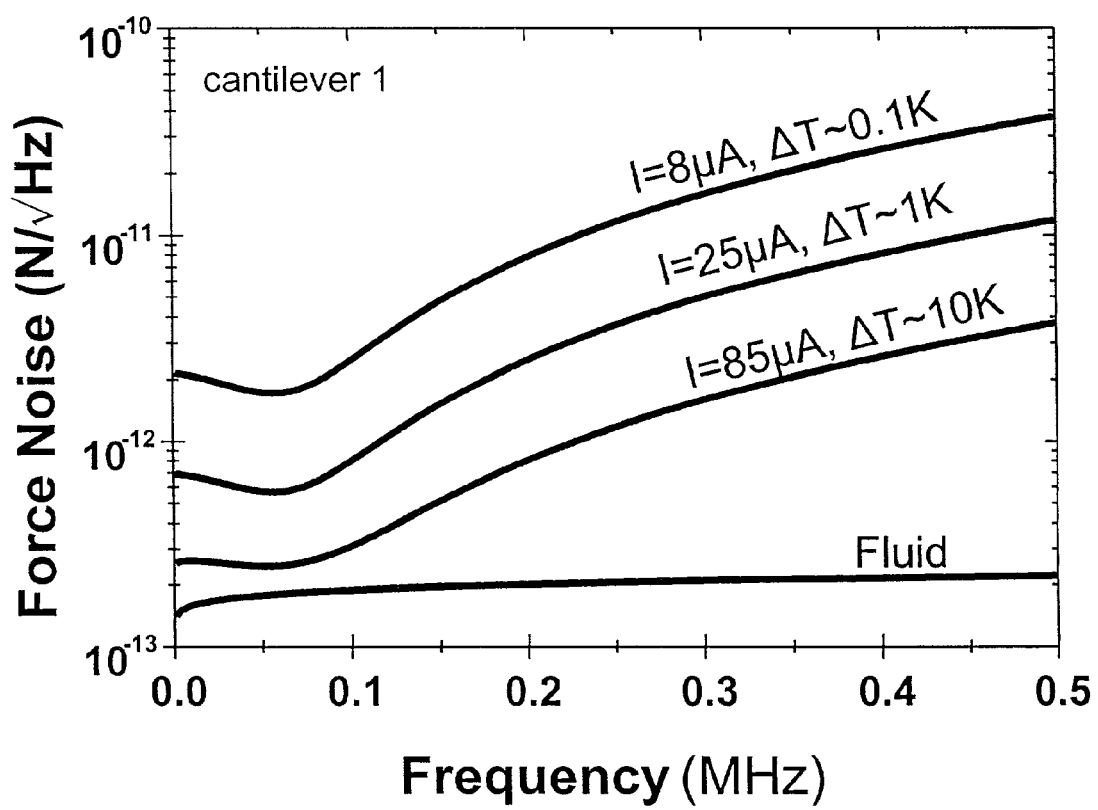
FIG. 10 is a graphical representation of the detection properties of a prototype of a biofunctionalized nanoelectromechanical sensing device according to the present invention.
Figure 11:
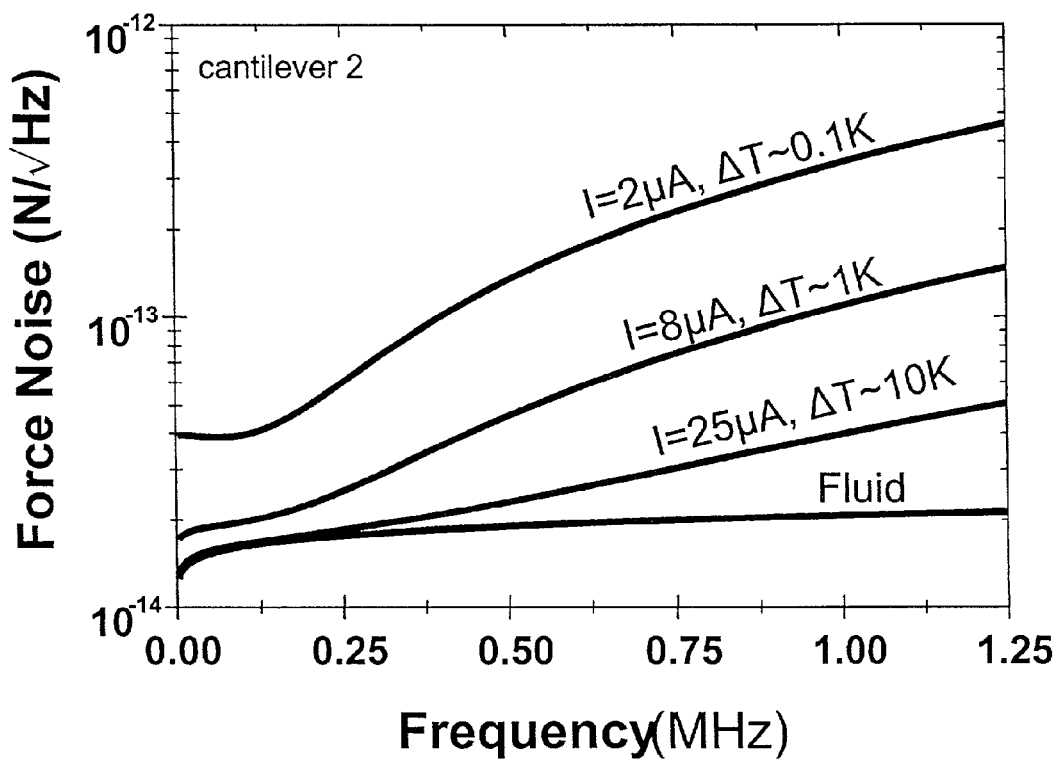
FIG. 11 is a graphical representation of the detection properties of a prototype of a biofunctionalized nanoelectromechanical sensing device according to the present invention.
Figure 12:
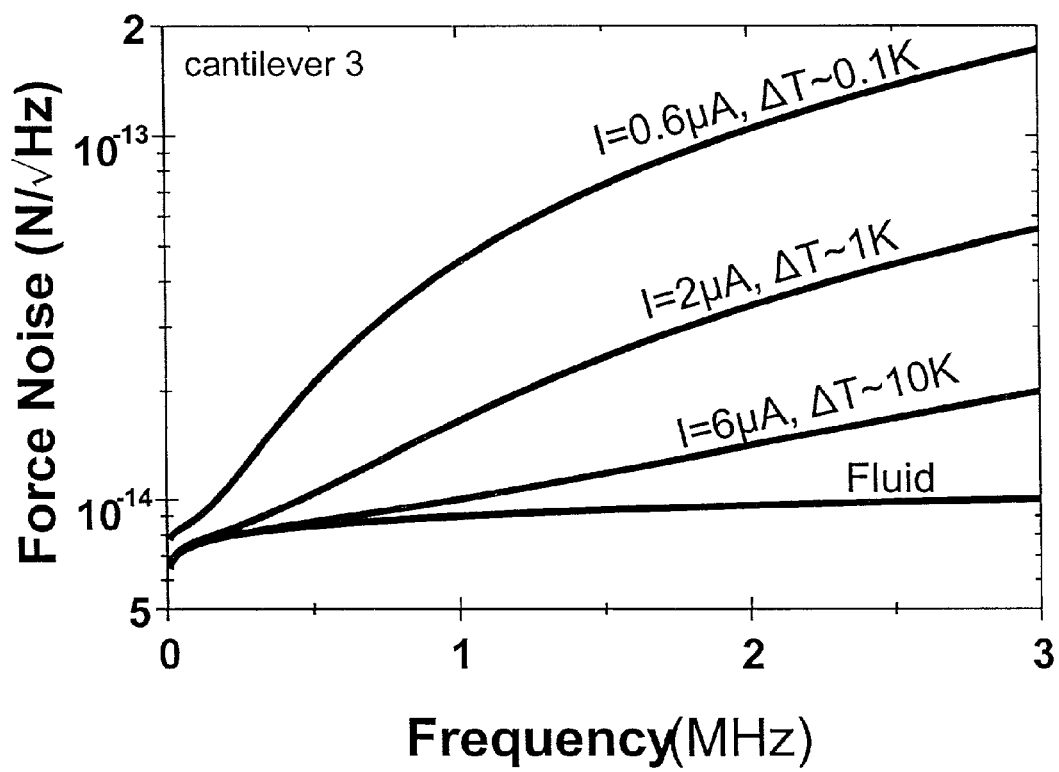
FIG. 12 is a graphical representation of the detection properties of a prototype of a biofunctionalized nanoelectromechanical sensing device according to the present invention.

In FIGS. 10 to 12 the coupled force sensitivity per unit bandwidth calculations for the three prototype notched vibrational cantilever resonators 1 to 3 in Tables 2 and 3 utilizing three different detector bias currents are plotted verse the thermal force noise of the solution. These calculations include the combined noise from fluidic, transducer, and readout amplifier sources.

FIG. 10 shows that for a temperature rise of 1K at the resonator tip, even the largest resonator (cantilever 1) yields a remarkably low coupled force sensitivity $[S_f^{(c)}]^{1/2} \leq 85$ fN/$\sqrt{Hz}$ for frequencies below 100 KHz. This indicates that a molecular detector utilizing the cantilever 1 resonator would be capable of taking dynamical measurements on the ~10 μs scale for absolute forces on the level of <30 pN without averaging.

FIG. 11, shows that for an 0.05K temperature rise at the tip of the resonator the cantilever 2 resonator device yields even better force sensitivity, $[S_f^{(c)}]^{1/2} \leq 20$ fN/$\sqrt{Hz}$ for frequencies below 0.5 MHz (10% above the fluidic fluctuation limit). This indicates that a molecular detector utilizing the cantilever 2 resonator would be capable of taking dynamical measurements on the ~2 μs scale for absolute forces on the level of <15 pN without averaging.

Finally, FIG. 12, shows the attainable force sensitivity for a device utilizing a cantilever 3 resonator. Again, for an 0.05K temperature rise at the tip of the resonator the cantilever 3 resonator device yields a force sensitivity of $[S_f^{(c)}]^{1/2} \leq 10$ fN/$\sqrt{Hz}$ for frequencies below 2 MHz (10% above the fluidic fluctuation limit) and the force sensitivity rises to just ~11 fN/$\sqrt{Hz}$ for frequencies $\leq 3$ MHz. This indicates that a molecular detector utilizing the cantilever 2 resonator would be capable of taking dynamical measurements on the ~300 ns scale for absolute forces on the level of <20 pN without averaging.

Accordingly, the achievable coupled sensitivity for the molecular detector described herein, as low as ~8 fN/$\sqrt{Hz}$, is limited predominantly by the fluidic fluctuations of the solution. As shown in Table 4, below, this threshold detection limit is well below the interaction forces of interest in most biological and chemical processes.

TABLE 4

| Interaction Forces | |
|---|---|
| Nature of Interaction | Interaction Force |
| Receptor/Ligand Interaction | 50-250 pN |
| Avidin-Biotin | 90-260 pN |
| Antibody-Antigen | 50-300 pn |
| Cadherin-Cadherin | 35-55 pN |
| DNA Hybridization | 65 pN-1.5 nN |
| Chemical Bond | 1-10 nN |
| Covalent (C—C, C—O, C—N) | 4.0-4.5 nN |
| Covalent (Au—S, Si—C) | 1-3 nN |

TABLE 4-continued

Interaction Forces

| Nature of Interaction | Interaction Force |
|---|---|
| H-bond | 10 pN |
| Unfolding Forces | 100-300 pN |
| Protein (Titin) unfolding | 150-300 pN |
| Dexran bond twists | 100-300 pN |

Figure 13:
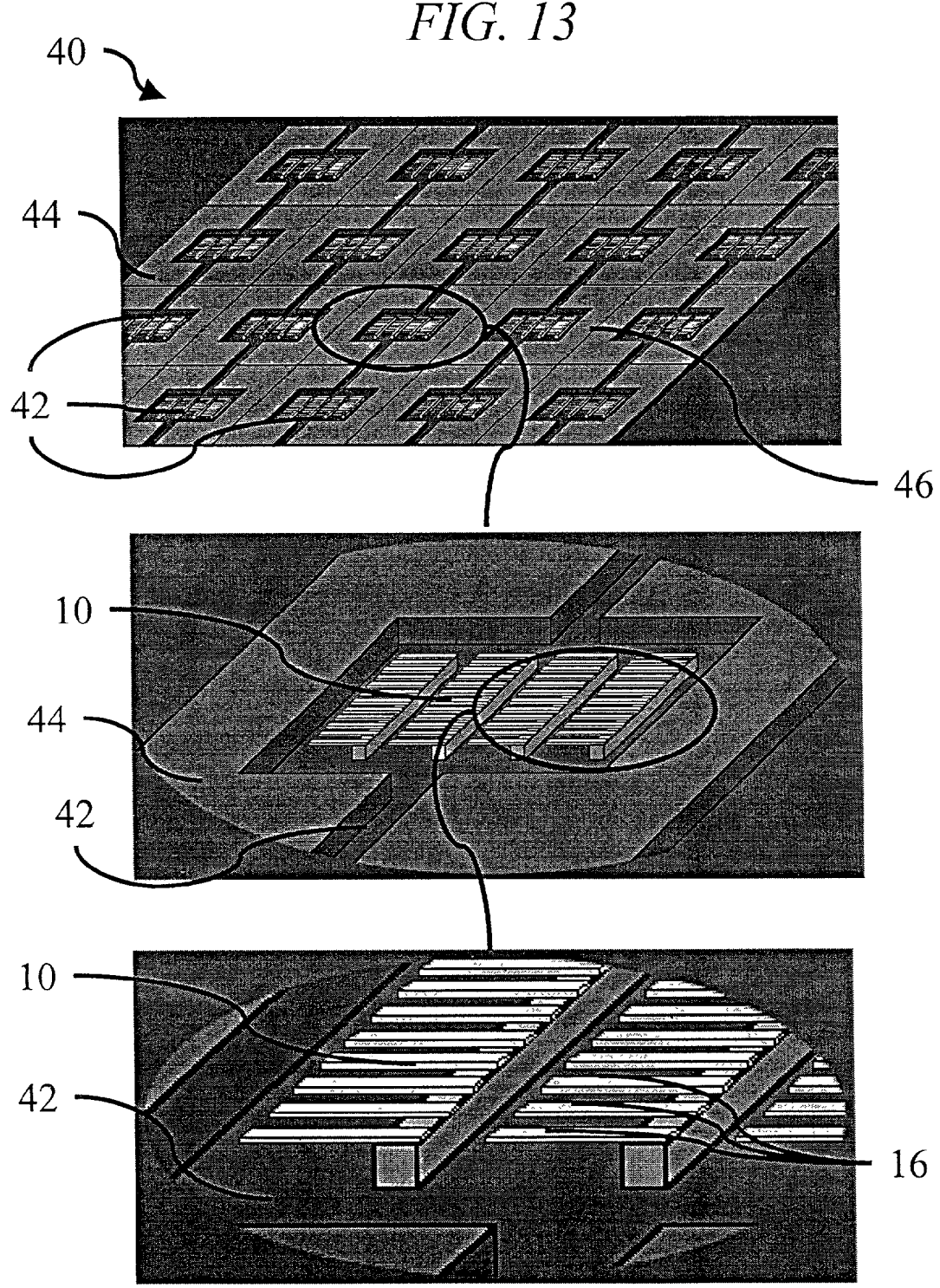
FIG. 13 is a schematic depiction of a second embodiment of a system of biofunctionalized nanoelectromechanical sensing devices according to the present invention.

Although only molecular detectors 10 having single resonator assemblies 16 are shown in the Figures and discussed in the text above, the molecular detector 10 according to the present invention may also comprise a large array or system of resonator assemblies. One exemplary embodiment of such a system is shown schematically in FIG. 13, which shows a multiple channel array 40 of molecular detectors 10, in which the array channels 42 are aligned in parallel on a single substrate 44 such that multiple or parallel processing of molecular samples can be carried out at one time. In this embodiment, multiple molecular detectors 10 are utilized for analysis of the molecules. It should be understood that while parallel and single array channels 42 are shown in FIG. 13, any suitable alternative geometry of channels 42 may be utilized such as, for example, folded channels may be used to increase the length of the detector path without increasing the size of the array body 40. Although the embodiment shown in FIG. 13 discloses a multi-channel array 40 in which the detector channels 42 are separated by walls 46, the multi-channel detector array 40 could alternatively comprise a single "sheet" of detector arrays without walls between the channels 42.

Further, while all of the resonators 16 of the molecular detector array system 40 could be functionalized to monitor for a single substance, as described in the previous embodiments, thereby providing greatly enhanced detector sensitivity, the resonators 16 of the detector array 40 system shown in FIG. 13 may also comprise individually biofunctionalized resonators such that multiple substances can be identified and monitored simultaneously. In addition, any combination of the various resonator embodiments shown and discussed in relation to FIGS. 3a to 3f, above, may be utilized in the molecular detector array system of the present invention.

Although specific embodiments are disclosed herein, it is expected that persons skilled in the art can and will design alternative molecular detectors, methods to produce the molecular detectors and/or molecular detector systems that are within the scope of the following claims either literally or under the Doctrine of Equivalents.

What is claimed is:

1. A molecular detector capable of detecting an analyte in solution comprising:
a solution reservoir;
at least one first nanometer-scale mechanical resonator which is disposed within the reservoir, wherein the at least one first resonator is biofunctionalized with a first receptor or a first ligand;
a substrate or a second mechanical resonator which is disposed within the reservoir, wherein the substrate or the second resonator is biofunctionalized with a second receptor or a second ligand, and wherein the first receptor or ligand and the second receptor or ligand are capable of binding to the analyte in solution such that the analyte binds to both the first receptor or ligand and to the second receptor or ligand at a same time; and
a detector in signal communication with the at least one first resonator for measuring a mechanical displacement of the resonator for detection of the analyte.

2. A molecular detector as described in claim 1, wherein the at least one first resonator comprises a resonator selected from the group consisting of: vibrational resonators, rotational resonators, torsional resonators and composite resonators.

3. A molecular detector as described in claim 1, wherein the at least one first resonator is a notched vibrational cantilever.

4. A molecular detector as described in claim 1, wherein the at least one first resonator is biofunctionalized with the first receptor.

5. A molecular detector as described in claim 1, wherein the at least one first resonator is made from a material selected from the group consisting of: silicon oxide, silicon, silicon carbide and gallium arsenide.

6. A molecular detector as described in claim 1, wherein the detector is integral with the at least one first resonator.

7. A molecular detector as described in claim 1, wherein the detector is a piezoresistive transducer.

8. A molecular detector as described in claim 7, wherein the transducer is made of p+ doped silicon.

9. A molecular detector as described in claim 1, wherein the detector is an optical detector.

10. A molecular detector as described in claim 1, wherein the detector is a lock-in detector.

11. A molecular detector as described in claim 1, wherein the at least one first resonator has a thickness between about 10 nm and 1 µm, a width between about 10 nm and 1 µm, and a length between about 1 µm and 10 µm.

12. A molecular detector as described in claim 1, wherein the at least one first resonator has a resonance motion vacuum frequency between about 0.1 and 12 MHz.

13. A molecular detector as described in claim 1, wherein the at least one first resonator has a force constant between about 0.1 mN/m and 1 N/m.

14. A molecular detector as described in claim 1, wherein the at least one first resonator has a Reynolds number between about 0.00 1 and 2.0.

15. A molecular detector as described in claim 1, wherein the at least one first resonator has a mass loading coefficient between about 0.3 and 11.

16. A molecular detector as described in claim 1, having a force sensitivity of about $8fN/\sqrt{Hz}$ or greater.

17. A molecular detector as described in claim 1, wherein the at least one first resonator is biofunctionalized to detect a receptor/ligand interaction.

18. A molecular detector as described in claim 1, wherein the at least one first resonator is biofunctionalized to detect DNA hybridization.

19. A molecular detector as described in claim 1, wherein the at least one first resonator is biofunctionalized to detect a chemical bond.

20. A molecular detector as described in claim 1, wherein the at least one first resonator is biofunctionalized to detect protein unfolding.

21. A molecular detector as described in claim 1, wherein the detector is a detector which is adapted to measure a change in damping of resonance motion of the at least one first resonator in response to a molecular binding event on the at least one first resonator.

22. A molecular detector as described in claim 1, wherein the at least one first resonator comprises a cantilever having at least two dimensions of one micron or less.

23. A molecular detector as described in claim 1, wherein the at least one first resonator is biofunctionalized with the first receptor and the substrate is biofunctionalized with the second ligand.

24. A molecular detector as described in claim 1, further comprising a driving element capable of mechanically displacing the first resonator at a chosen frequency.

25. A molecular detector as described in claim 1, wherein the detector comprises a piezoresistive detector layer which is located on the at least one resonator.

26. A molecular detector as described in claim 1, wherein the substrate is disposed in the reservoir.

* * * * *